(12) United States Patent
Yu

(10) Patent No.: US 10,934,513 B2
(45) Date of Patent: Mar. 2, 2021

(54) FULLY AUTOMATED CONTINUOUS CELL CULTURE SYSTEM

(71) Applicant: Shanghai GenBase Biotechnology Co., Ltd., Shanghai (CN)

(72) Inventor: Xuejun Yu, Shanghai (CN)

(73) Assignee: SHANGHAI GENBASE BIOTECHNOLOGY CO., LTD., Shanghai (CN)

( * ) Notice: Subject to any disclaimer, the term of this patent is extended or adjusted under 35 U.S.C. 154(b) by 178 days.

(21) Appl. No.: 16/064,414

(22) PCT Filed: Dec. 15, 2016

(86) PCT No.: PCT/CN2016/110035
§ 371 (c)(1),
(2) Date: Oct. 5, 2018

(87) PCT Pub. No.: WO2017/107837
PCT Pub. Date: Jun. 29, 2017

(65) Prior Publication Data
US 2019/0017009 A1  Jan. 17, 2019

(30) Foreign Application Priority Data

Dec. 23, 2015 (CN) .......................... 2015 1 0981648
Dec. 23, 2015 (CN) .......................... 2015 1 0981653
(Continued)

(51) Int. Cl.
*C12M 3/00* (2006.01)
*C12M 1/00* (2006.01)
(Continued)

(52) U.S. Cl.
CPC ............ *C12M 27/16* (2013.01); *C12M 23/00* (2013.01); *C12M 23/14* (2013.01); *C12M 23/20* (2013.01);
(Continued)

(58) Field of Classification Search
CPC ....... C12M 23/14; C12M 27/16; C12M 27/10
See application file for complete search history.

(56) References Cited

U.S. PATENT DOCUMENTS

2005/0105172 A1* 5/2005 Hasegawa .............. C12M 23/50
359/368
2010/0190245 A1* 7/2010 Hui ........................ C12M 23/02
435/325
(Continued)

FOREIGN PATENT DOCUMENTS

CN         1678751 A      1/2005
CN       102086438 A      6/2011
(Continued)

OTHER PUBLICATIONS

English translation of CN 102086438 to Han et al (generated 2020).*

*Primary Examiner* — Nathan A Bowers
(74) *Attorney, Agent, or Firm* — Global IP Services; Tianhua Gu

(57) ABSTRACT

The invention provides a full-automatic cell culture system, at least comprising: a control module, a control platform, a dark field microscope for on-line observation of cell culture, a cell incubator shaker and a cell culture bag. The control platform is connected to the dark field microscope for on-line observation of cell culture and the cell incubator shaker respectively, and the control module is connected to the control platform. The invention also provides a culture bag support frame for a continuous cell incubator shaker, the continuous cell incubator shaker, a non-contact sensor con- (Continued)

nector, the cell culture bag and the dark field microscope for on-line observation of cell culture which are related to the full-automatic cell culture system, thereby realizing continuous culture and observation of cells.

28 Claims, 16 Drawing Sheets

(30) Foreign Application Priority Data

| | | | |
|---|---|---|---|
| Mar. 8, 2016 | (CN) | ............................ | 2016 1 0131141 |
| Mar. 8, 2016 | (CN) | ............................ | 2016 1 0131142 |
| May 16, 2016 | (CN) | ............................ | 2016 1 0325563 |
| May 16, 2016 | (CN) | ............................ | 2016 1 0325576 |

(51) Int. Cl.
  *C12M 3/06* (2006.01)
  *C12M 1/34* (2006.01)
  *C12M 1/02* (2006.01)
  *G02B 21/10* (2006.01)
  *G02B 21/26* (2006.01)

(52) U.S. Cl.
  CPC ............ *C12M 23/22* (2013.01); *C12M 23/48* (2013.01); *C12M 41/00* (2013.01); *C12M 41/22* (2013.01); *C12M 41/26* (2013.01); *C12M 41/34* (2013.01); *C12M 41/36* (2013.01); *C12M 41/44* (2013.01); *G02B 21/10* (2013.01); *G02B 21/26* (2013.01)

(56) References Cited

U.S. PATENT DOCUMENTS

| | | | |
|---|---|---|---|
| 2013/0038727 A1* | 2/2013 | Clark | ..................... C12M 41/48 |
| | | | 348/143 |
| 2014/0011270 A1* | 1/2014 | Chotteau | ................. C12M 27/20 |
| | | | 435/326 |
| 2017/0036181 A1* | 2/2017 | Boettcher | ............... A61M 5/44 |
| 2017/0044481 A1* | 2/2017 | Kawano | ................. H04N 5/232 |
| 2017/0261732 A1* | 9/2017 | Takahashi | .............. G02B 21/06 |
| 2018/0127696 A1* | 5/2018 | Takeuchi | ............... C12M 23/42 |
| 2018/0251722 A1* | 9/2018 | Patil | ....................... C12M 23/02 |

FOREIGN PATENT DOCUMENTS

| | | |
|---|---|---|
| CN | 102762713 A | 10/2012 |
| CN | 203382764 U | 1/2014 |
| CN | 204439923 U | 7/2015 |
| CN | 105385587 A | 3/2016 |
| CN | 105385597 A | 3/2016 |
| CN | 105567565 A | 5/2016 |
| CN | 105567566 A | 5/2016 |
| CN | 105785560 A | 7/2016 |
| CN | 105925481 A | 9/2016 |
| WO | WO 2006001716 | 1/2006 |
| WO | WO 2006051813 | 5/2006 |

\* cited by examiner

FULLY AUTOMATED CONTINUOUS CELL CULTURE SYSTEM

CROSS REFERENCE TO RELATED PATENT APPLICATION

The present application is the US national stage of PCT/CN2016/110035 filed on Dec. 15, 2016, which claims the priorities of the CN2015109816486 filed on Dec. 23, 2015, CN2015109816537 filed on Dec. 23, 2015, CN2016101311420 filed on Mar. 8, 2016, CN2016101311416 filed on Mar. 8, 2016, CN2016103255764 filed on May 16, 2016 and CN2016103255637 filed on May 16, 2016, which applications are incorporated herein by reference.

TECHNICAL FIELD

The present invention relates to a full-automatic continuous cell culture system, which is mainly configured to culture and observe cells.

BACKGROUND

At present, the immune cell used for human body treatment is mainly cultured in a cell culture dish or a cell culture flask under a laboratory clean bench, and according to the density of cell growth, continuous bottle separation culture is performed. Such cell culture mode is not only time-consuming and labor-consuming, but also relatively easy to cause contamination due to the need for different bottle separation and sample addition.

ZL2007200130617 discloses a microbial incubator shaker, comprising a shaker, a motor and a deceleration mechanism. The shaker is assembled on the guide rail through a roller. The shaker is hinged to one end of a rocker arm, and the other end of the rocker arm is hinged on the eccentric shaft of a disc. The central axis of the disc is connected to a power output shaft of the reduction mechanism. The disc design of the shaker is not suitable for continuous cell culture.

ZL2013102727942 discloses an amplitude-variable rotary type cell incubator shaker, comprising an eccentric device, a tray, a storage vessel, a base, a motor, counter weights and a controller, wherein the eccentric device is mounted on the base, the eccentric device comprises a main eccentric wheel and a secondary eccentric wheel, the main eccentric wheel and the secondary eccentric wheel are provided with the counter weights, the tray is disposed above the secondary eccentric, the motor is connected to one set of eccentric device by a transmission device, and such set of eccentric device comprises: the main eccentric wheel, an amplitude changing wheel, an amplitude changing rod and an amplitude positioning plate. The amplitude positioning plate is disposed on the main eccentric wheel, the amplitude changing wheel is connected on the amplitude positioning plate by the amplitude changing rod, the upper end of the amplitude changing wheel is connected on the tray, and the motor is connected to the controller. Although the shaker can realize the amplitude changing operation, its tray design is not suitable for the continuous culture of cells.

The invention CN2014103149910 discloses an oscillating shaker, comprising: a rack, an oscillating box, a motor, a belt, a belt wheel, a synchronous wheel, a synchronous belt, an eccentric shaft, an oscillating plate, a pulley, a guide rail and a main shaft, wherein the oscillating box is disposed below the rack, the motor is disposed on one side of the oscillating box, the main shaft is disposed in the center of the rack, the belt wheel and the synchronous wheel are disposed below the main shaft, the belt is disposed on the belt wheel and connected with the motor, the synchronous belt is disposed on the synchronous wheel, the other end of the synchronous belt is connected with the eccentric shaft, an eccentric wheel is connected on the upper end of the main shaft, the oscillating plate is fixed on the eccentric wheel, the oscillating box is fixed under the oscillating plate, and the guide rail and the pulley are disposed under the oscillating box. Although the operating area of the shaker is increased, and the efficiency is improved, the design of the oscillating plate thereon is not suitable for the continuous culture of the cells either.

Meanwhile, at present, the methods used by the laboratory for observing cells are still relatively primitive, most of them involve the link of sampling and preparation of specimens, the operation is relatively complicated, continuous and real-time observation of the cells cannot be achieved. The cell is traditionally cultured in a carbon dioxide incubator with the culture dish or culture flask, the requirements on culture conditions are relatively high, the operation needs to be performed under the super-clean bench, then the cells are placed in the carbon dioxide incubator for culture, and the cells are taken out at proper time and placed under a microscope for observation of a cell growth state.

For the measurement on a pH value and a dissolved oxygen amount in the culture solution during the cell culture process, contact detection is generally required, which easily causes contamination. Even with strict aseptic procedures, it is very difficult to avoid the contamination of the cells, especially when human immune cells for clinical research or clinical treatment are cultured. Once the cells are contaminated, not only the cell culture is affected, but also the life of a patient is threatened.

In addition, for the dark field microscope, the illuminating light rays are shifted without entering an objective lens by using a special dark field condenser mainly, and only the scattered light of a sample enters the objective lens. Therefore, a bright image is obtained on a dark background. In contrast to the dark field illumination, the illuminating light rays directly reach an imaging plane, which is called as bright field illumination.

The Tyndall phenomenon refers to that an illuminating light pillar can be seen from the side surface of a light beam when the condensing light beam is incident to sol. In the propagation process of the light, when the light rays illuminate particles, if the diameter of the particles is slightly smaller than a wavelength of the incident light, light scattering will occur, each particle becomes an illuminating point, and the light pillar can be seen from the side surface.

The dark field microscope just uses the above principle. The special optical configuration of the dark field microscope enables the illuminating incident light to not enter the objective lens, but the sample is illuminated and emits reflected light. During the microscopic examination, since the illuminating light rays cannot be directly observed, the planar visual field perpendicular to an optical axis is dark, the bright object image formed by the scattered light and the reflected light can be clearly seen on the dark background, and great contrast is caused between the object image and the background. The sample in the visual field is illuminated by oblique light rays, the light rays can be scattered and reflected from various structural surfaces of the sample, and the bright contours of many organelles, such as the cell nucleuses, mitochondria, vacuoles, and certain inclusions can be seen. If it is the cell being divided, various types of spindle fibers and chromosomes can also be seen.

However, currently, most dark field microscopes have the following problems: at first, in general cases, the user have to extract the specimen, and then place it on a slide glass, and place it under the objective lens before observing, the operations are very tedious, and are not convenient for observation at real time.

With the development of science and technology and the advancement of artificial intelligence, people have paid attention to continuous culture and observation of the cells. However, there has not been a device that can realize continuous culture and observation of the cells yet.

SUMMARY

In order to overcome the defects in prior art, an objective of the present invention is: to provide a culture bag support frame capable of being used for continuous cell culture according to different requirements of cell culture. The culture bag support frame according to the present invention can be matched with an arc-shaped 3D culture bag for use, and meets various requirements of continuous cell culture.

A second objective of the present invention is: to provide an incubator shaker capable of being for continuous cell culture. The shaker according to the present invention can be matched with the arc-shaped 3D culture bag for use, and meets various requirements of continuous cell culture.

A third objective of the present invention is: to provide a non-contact sensor connector and application in combination with various conditions of cell culture in view of various risk factors existing in the process of cell culture, the contact with a sample is not required, and relative indexes of cell culture fluid are monitored in real time.

A fourth objective of the present invention is: to provide a full-closed 3D cell culture bag without the need of exposure from the initial culture to the ending of culture of the cells in combination with various conditions of cell culture in view of various risk factors existing in the process of cell culture.

A fifth objective of the present invention is: to provide an efficient dark field microscope capable of realizing real-time observation and configured for cell culture.

A sixth objective of the present invention is: to provide a full-automatic continuous cell culture system, which can realize continuous culture and observation of the cells, and the determination on various parameters of the culture fluid.

The present invention firstly provides a culture bag support frame for continuous cell culture, which comprises an arc-shaped bottom plate and cell culture bag fixing parts, wherein the arc-shaped bottom plate is provided with one or more accessory fixing hole positions.

Preferably, the accessory fixing hole positions are internally provided with internal threads for better fixing external accessories.

Preferably, the arc-shaped bottom plate is provided with an object lens inserting gap.

Preferably, the edge of the arc-shaped bottom plate is provided with baffles.

Preferably, the arc-shaped bottom plate is further provided with a heating plate.

Preferably, the heating plate is a temperature control heating plate, and the temperature control heating plate is usually provided with a heating part and a temperature measuring element thereon. The temperature control heating belongs to the prior art.

The cell culture bag fixing parts may be disposed on each of both sides of the arc-shaped bottom plate and may comprise platforms extending from two sides of the arc-shaped bottom plate in horizontal direction, and the platforms are provided with a parts matched with the fixing parts on a cell bag.

The culture bag support frame for continuous cell culture according to the present invention can be matched with a three-dimensional cell culture bag for use, can meet the requirements of heating and sample adding during continuous cell culture and the mounting requirements of other cell culture detection devices, realizes the continuous cell culture and has smaller damage to the cells during the cell culture.

According to a second aspect of the present invention, there is a provided a continuous cell incubator shaker.

The continuous cell incubator shaker according to the present invention comprises a culture bag support frame, a swing frame and a shake device, wherein the culture bag support frame is provided with an arc-shaped bottom plate and cell culture bag fixing parts, the swing frame comprises a swing base, the swing base is provided with support arms, the culture bag support frame and the swing frame are fixedly connected by the support arms, the shake device comprises a substrate, the substrate is provided with swing components, and the swing base is connected to the swing components.

The arc-shaped bottom plate may be provided with one or a plurality of accessory fixing hole positions.

Preferably, internal threads are disposed in the fixing holes to better fix external accessories. Spaces for mounting or inserting external accessories are provided below the accessory fixing hole positions.

Preferably, the arc-shaped bottom plate is provided with a heating plate.

Preferably, the arc-shaped bottom plate is provided with an object lens inserting gap.

Further preferably, the edge of the arc-shaped bottom plate is provided with baffles.

The swing components may be any mechanism capable of realizing a swing action.

Specifically, the swing components may comprise hinging seats and at least one vertical reciprocating movement mechanism, the hinging seats is disposed on the substrate, the swing base is hinged to the hinging seats, and the vertical reciprocating movement mechanism is connected to or abutted against the swing base.

The vertical reciprocating movement mechanism may be various existing mechanisms capable of realizing reciprocating motion, for example, an electric push rod, a linear motor, a crankshaft connecting rod mechanism, etc.

The cell culture shaker according to the present invention can meet the heating, shaking and sample adding during cell culture as well as mounting of other cell culture detection devices, and the continuous cell culture is realized.

According to a third aspect of the present invention, there is provided a non-contact sensor connector, comprising a basal disc and an open cavity for containing sensor probe, the basal disc is provided with a transparent partition, the cavity containing sensor probe and the basal disc are connected and are located on one side of the transparent partition, and the other side of the transparent partition is provided with a converting film.

Preferably, the transparent partition is colorless, and both side surfaces are smooth.

The sensor probe containing cavity may be inserted with or in threaded connection with a sensor probe.

Preferably, internal threads are disposed in the cavity containing sensor probe.

The converting film is a pH-induced color change film or dissolved oxygen-induced color change film.

Further preferably, a flange protruding out of the basal disc is disposed on the outer edge of the side surface of the transparent partition provided with the converting film.

The sensor probe containing cavity and the basal disc may be in fixed or detachable connection. The detachable connection manner comprises but not limited to insertion, threaded connection, etc.

Preferably, a joint between the sensor probe containing cavity and the basal disc is in smooth transition.

The non-contact sensor connectors according to present invention can be configured for a closed cell culture device.

The cell culture device comprises but not limited to a cell culture bag.

Due to the design of the non-contact sensor connector according to the present invention, a sensor matched therewith has no need of sterilization and disinfection, and not only is the operation more convenient, but also the contamination can be better prevented.

According to a fourth aspect of the present invention, there is provided a cell culture bag, comprising a closed bag body and fixing parts on both sides of the bag body, wherein the top surface of the closed bag body is provided with an external liquid adding port, an external liquid injecting port, a gas inlet and a gas outlet, the bottom surface of the closed bag body is provided with a liquid recycling port and at least one sensor connector, and each of the external liquid adding port, the external liquid injecting port, the gas inlet, the gas outlet, and the liquid recycling port is provided with an aseptic quick connector.

In a preferred embodiment, materials of the closed bag body have a multilayer composite structure.

In a preferred embodiment, the closed bag body is a three-dimensional bag cavity defined by an upper bag piece, a lower bag piece, a left side bag piece and a right side bag piece.

More preferably, the lower bottom sides of the left side bag piece and the right side bag piece are arc-shaped. In a preferred embodiment, the left side bag piece and the right side bag piece are both oval, and the upper bag piece and the lower bag piece are rectangular.

Further, the middle of the bottom of the bag body is provided with a transparent observation area. The transparent observation area is disposed on the bottom of the cell culture bag, and a cell morphology observing device may be disposed on the culture platform to directly observe a cell condition in the cell culture bag from the bottom.

One or more sensor connectors may be disposed. Preferably, two sensor connectors are disposed, wherein one sensor connector is the sensor connector configured to be connected to a pH value sensor probe, and the other sensor connector is the sensor connector configured to be connected with a dissolved oxygen (DO) sensor probe.

The sensor connectors may be non-contact sensor connectors or contact sensor connectors. In preferred embodiments, the sensor connectors are the non-contact sensor connectors, i.e., after the sensor probe is inserted into the sensor connector, the probe makes no contact with the culture fluid in the bag body.

The cell culture bag according to the present invention can be configured for cell culture.

The cell culture bag according to the present invention has the following beneficial effects:

1. The cell culture bag according to the present invention is unique in structure and can meet the continuous sample adding culture under the condition of less culture fluid, till the culture requirements are met.

2. According to the 3D irregular-shaped cell culture bag designed in the present invention, in the process of cell culture, a shearing force generated by shaking of the culture platform is minimal, and the damage of the shearing force to the cells is also minimal.

3. All connectors of the cell culture bag according to the present invention adopt an aseptic quick connection manner, thereby reducing the risk of cell contamination caused by culture operation to the greatest extent.

4. The volume of the cell culture bag according to the present invention can be infinitely expanded according to a required culture amount.

According to a fifth aspect of the present invention, there is provided a dark field microscope for on-line observation of cell culture, which comprises an illuminating element, a movable support, a support base, an object lens, a photosensitive element, a pipe diameter unit, an A/D converting unit, a power module and a control system, wherein the illuminating element is disposed on the top of the movable support, the movable support is disposed on the support base, the pipe diameter unit is connected on the lower part of the movable support, the object lens is disposed on the pipe diameter unit and is correspondingly disposed below the illuminating element, the photosensitive element is disposed in the pipe diameter unit and configured to collect a light source signal on the object lens, the A/D converting unit is connected to the photosensitive element, the control system is connected to the A/D converting unit, and the power source module is configured to provide electricity for the dark field microscope for on-line observation of cell culture.

Preferably, the illuminating element comprises a round lamp holder, and a plurality of illuminating lamps disposed on the lamp holder and arranged as a plurality of concentric circles, and centers of circles of the concentric circles have the same position as the center of circle of the lamp holder.

Preferably, a distance from the lamp holder to the object lens is 10-30 cm.

Preferably, light sources of the illuminating lamps and the object lens form a dark field, and illuminating needs of the dark field are met.

Preferably, the illuminating lamps are LED lamps.

Preferably, the support base comprises a step-motor, a slide mechanism and a base, wherein the slide mechanism comprises a slide block and a slide rail, preferably, the control system is connected to and controls the step-motor, the step-motor is connected to the slide block, the slide block is slidably connected on the base by the slide rail and can move horizontally, and the movable support is disposed on the slide block.

Preferably, the pipe diameter unit is slidably connected on the movable support, the part of the pipe diameter unit connected to the movable support is provided with a chute, and the pipe diameter unit can slide up and down along the chute.

Preferably, the control system comprises:

a movable support control unit, configured to control the movement of the movable support;

an illuminating element control unit, configured to control the illuminating element to be ON or OFF;

a checking unit, configured to check content observed by the object lens under a current state; and a memory unit, configured to store the observed content which needs to be stored.

Preferably, the movable support has a hollow structure, and the movable support control unit is disposed in the hollow structure.

Preferably, the photosensitive element is a CCD sensor.

The dark field microscope for on-line observation of cell culture according to the present invention can be applied to observation on the cells in the cell culture bag in cell culture.

The dark field microscope for on-line observation of cell culture according to the present invention has the following beneficial effects:

The device can be adopted to realize continuous and repeated observation of a sample without repeatedly sampling, when the sample is observed every time, the sample can be placed between the photosensitive element and the object lens by moving the movable support through the control system, and the operation is more convenient and faster. Meanwhile, the damage to the sample caused when a microscopic sample is manufactured is reduced, such that detection result is more accurate.

According to a sixth aspect of the present invention a full-automatic cell culture system is provided, which at least comprises a control module, a control platform, a dark field microscope for on-line observation of cell culture, a cell incubator shaker, a cell culture bag and a power source module; wherein the cell incubator shaker comprises a culture bag support frame, a swing frame and a shake device, the culture bag support frame is provided with an arc-shaped bottom plate and cell culture bag fixing parts, the swing frame comprises a swing base, the swing base is provided with support arms, the culture bag support frame and the swing frame are fixedly connected by the support arms, the shake device comprises a substrate, the substrate is provided with swing components, the swing base is connected to the swing components, and the arc-shaped bottom plate is provided with an object lens inserting gap;

the cell culture bag comprises a closed bag body, and the middle of the bottom surface of the bag body is provided with a transparent observation area; and the bag body is disposed on the cell incubator shaker, and the transparent observation area is matched with the object lens inserting gap;

the dark field microscope for on-line observation of cell culture comprises an object lens, and the object lens can be inserted into the object lens inserting gap in the cell incubator shaker;

the control platform is connected to the dark field microscope for on-line observation of cell culture and the cell incubator shaker respectively;

the control module is connected to the control platform; and the power source provides electricity for the system.

In order to further optimize the design solution, the dark field microscope for on-line observation of cell culture comprises an illuminating element, a movable support, a support base, a photosensitive element, a pipe diameter unit, an A/D converting unit, a power source module and a control module, wherein the illuminating element is disposed on the top of the movable support, the movable support is disposed on the support base, the pipe diameter unit is connected on the lower part of the movable support, the object lens is disposed on the pipe diameter unit and is correspondingly disposed below the illuminating element, the photosensitive element is disposed in the pipe diameter unit and configured to collect a light source signal on the object lens, the A/D converting unit is connected to the photosensitive element, the control module is connected to the A/D converting unit.

Preferably, the illuminating element comprises a round lamp holder, and a plurality of illuminating lamps disposed on the lamp holder and arranged as a plurality of concentric circles, and centers of circles of the concentric circles have the same position as the center of circle of the lamp holder.

Preferably, a distance from the lamp holder to the object lens is 10-30 cm.

Preferably, light sources of the illuminating lamps and the object lens form a dark field, and illuminating needs of the dark field are met.

Preferably, the illuminating lamps are LED lamps.

Preferably, the support base comprises a step-motor, a slide mechanism and a base, wherein the slide mechanism comprises a slide block and a slide rail, the control module is connected to and controls the step-motor, the step-motor is connected to the slide block, the slide block is slidably connected to the base by the slide rail and can move horizontally, the movable support is disposed on the slide block.

In order to further optimize the design solution, the arc-shaped bottom plate is provided with one or a plurality of accessory fixing hole positions, and spaces for mounting or inserting external accessories are provided below the accessory fixing hole positions.

Preferably, the arc-shaped bottom plate is provided with a heating plate.

Preferably, the edge of the arc-shaped bottom plate is provided with baffles.

Preferably, the cell culture bag fixing parts are disposed on two sides of the arc-shaped bottom plate and comprise platforms extending from two sides of the arc-shaped bottom plate in horizontal direction, and the platforms are provided with fixing rod clamps and/or fixing rod inserting mechanisms.

Preferably, the swing base is a flat plate and is provided with support arms on two ends, the culture bag support frame makes no contact with the swing base, and a clearance is provided therebetween for mounting or inserting the external accessory.

Preferably, the swing components comprise hinging seats and at least one vertical reciprocating movement mechanism, the hinging seats are disposed on the substrate, the swing base is hinged to the hinging seats, and the vertical reciprocating movement mechanism is connected to or abutted against the swing base.

In order to further optimize the design solution, the cell culture bag comprises fixing parts on both sides of the bag body, wherein the top surface of the closed bag body is provided with an external liquid adding port, an external liquid injecting port, a gas inlet and a gas outlet, the bottom surface of the closed bag body is provided with a liquid recycling port and at least one sensor connector, and each of the external liquid adding port, the external liquid injecting port, the gas inlet, the gas outlet, and the liquid recycling port is provided with an aseptic quick connector.

Preferably, the closed bag body is a three-dimensional bag cavity defined by an upper bag piece, a lower bag piece, a left side bag piece and a right side bag piece, the lower bottom sides of the left side bag piece and the right side bag piece are arc-shaped, the left side bag piece and the right side bag piece are oval, and the upper bag piece and the lower bag piece are rectangular.

Preferably, an innermost layer of the closed bag body is a polyethylene layer.

Preferably, materials of the closed bag body have a five-layer composite structure which comprises the polyethylene layer, an adhesive layer, an ethylene vinyl alcohol layer, another adhesive layer and another polyethylene layer from inside to outside in sequence.

Preferably, a number of sensor connector is one or more.

Preferably, the sensor connector is a non-contact sensor connector or a contact sensor connector.

Preferably, the non-contact sensor connector comprises a basal disc and a cavity containing sensor probe, the basal disc is provided with a transparent partition, the cavity containing sensor probe and the basal disc are connected and are located on one side of the transparent partition and the other side of the transparent partition is provided with a converting film.

Preferably, the converting film is a pH-induced color change film or dissolved oxygen-induced color change film.

In order to further optimize the design solution, the control platform comprises a control cabinet, and an automatic heating unit, a preheating bag and peristaltic pumps which are disposed on the control cabinet; the automatic heating unit comprises a preheating plate, the preheating bag is disposed on the preheating plate, the peristaltic pumps comprise a first peristaltic pump and a second peristaltic pump, the automatic heating unit further comprises a cell culture fluid tank body, the tank body is connected to a liquid inlet of the preheating bag by a first pipeline, an outlet of the preheating bag is communicated with the cell culture bag by a second pipeline, the first peristaltic pump is connected to the first pipeline, the second peristaltic pump is connected to the second pipeline, and the automatic heating unit, the first peristaltic pump and the second peristaltic pump are connected to the control module.

Preferably, a gas mixing unit is further disposed in the control cabinet, a gas outlet of the gas mixing unit is disposed in the control cabinet and is communicated with the cell culture bag by a third pipeline, a gas inlet of the gas mixing unit is connected to an external gas source, and the gas mixing unit is connected to the control module.

Preferably, the control cabinet is further provided with a pH value detection connector and a dissolved oxygen detection connector, as well as a pH value detection probe and a dissolved oxygen detection probe.

In order to further optimize the design solution, and realize the control of the control module over the culture system, the control module comprises:

a movable support control unit, configured to control the movable support to move;

an illuminating element control unit, configured to control the illuminating element to be ON or OFF;

a checking unit, configured to check content observed by the object lens under a current state, and respective parameters of a cell growth environment under the current state;

a memory unit, configured to store the observed content which needs to be stored and record the respective parameters of the cell growth environment;

a gas control unit, configured to control gases in the cell culture bag; and a cell culture fluid control unit, configured to control the temperature and supply of cell culture fluid.

The full-automatic continuous cell culture system according to the present invention can be configured for continuous cell culture.

The full-automatic continuous cell culture system and the improved solution according to the present invention have the following beneficial effects:

(1) The continuous cell culture is realized, and meanwhile, the continuous heating, shaking and sample adding are realized.

(2) Manual fluid change is not required, intelligent control over a temperature of the cell sap is realized and automatic fluid adding can be realized.

(3) The user can adjust the swing frequency and angle of the shaker according to a cell culture state, thereby ensuring that the cells are in the optimal growth environment.

(4) The detection on various parameters in the cell culture bag can be realized by the probes of various detectors.

(5) The cell sample can be observed by the dark field microscope without sampling, and continuous real-time observation of the cells can be realized.

(6) The cell culture bag is unique in structure and can meet the continuous sample adding culture under the condition of less culture fluid, till the culture requirements are met.

(7) According to the 3D irregular-shaped cell culture bag designed in the present invention, in the process of cell culture, a shearing force generated by shaking of the culture platform is minimal, and the damage of the shearing force to the cells is also minimal.

(8) The connectors of the cell culture bag adopt an aseptic quick connection manner, thereby reducing the risk of cell contamination caused by culture operation to the greatest extent.

(9) The volume of the cell culture bag can be infinitely enlarged according to a required culture amount.

(10) Various parameters in the cell growth process can be recorded and checked in real time.

(11) The gases required for cell culture can be intelligently provided.

The dotted line indicates a theoretically shielded bag piece at an illustrative angle.

Figure 13:
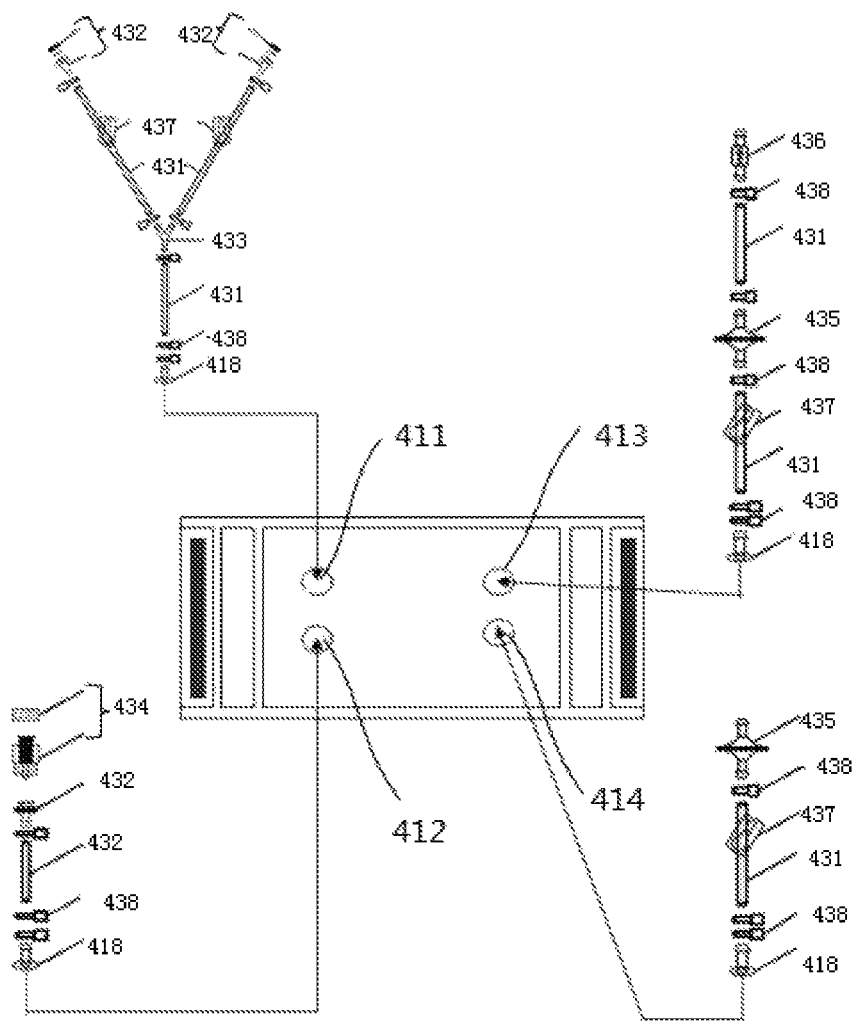

FIG. 13 shows a schematic diagram of a connecting pipeline on the top surface of a bag body under a use state of a cell culture bag according to an embodiment of the present invention.

Figure 14:
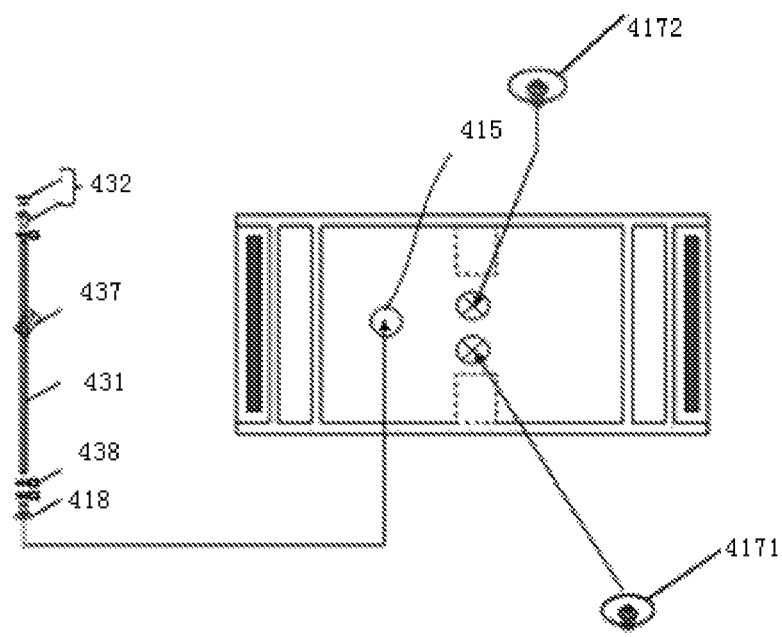

FIG. 14 shows a schematic diagram of a connecting pipeline on the bottom surface of a bag body under a use state of a cell culture bag according to an embodiment of the present invention.

Figure 15:
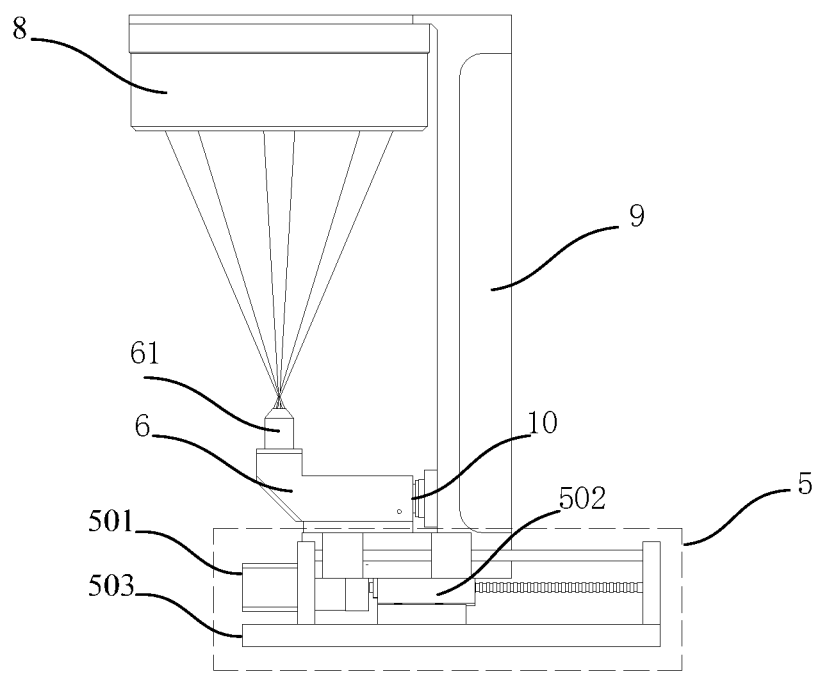

FIG. 15 shows a structural schematic diagram of a dark field microscope for on-line observation of cell culture in the present invention.

Figure 16:
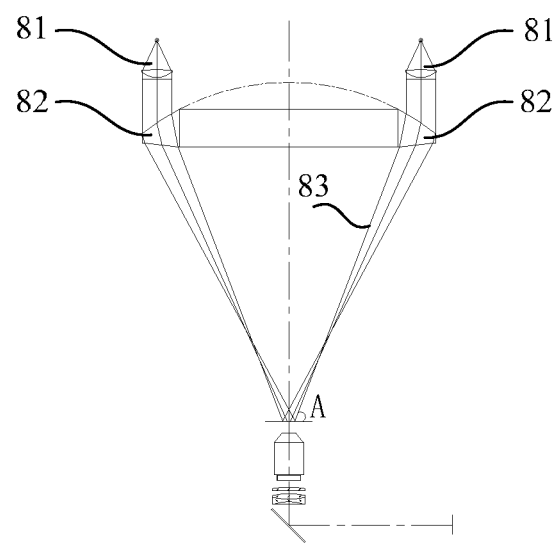

FIG. 16 shows a schematic diagram of an illuminating principle of a dark field in the present invention.

Figure 17:
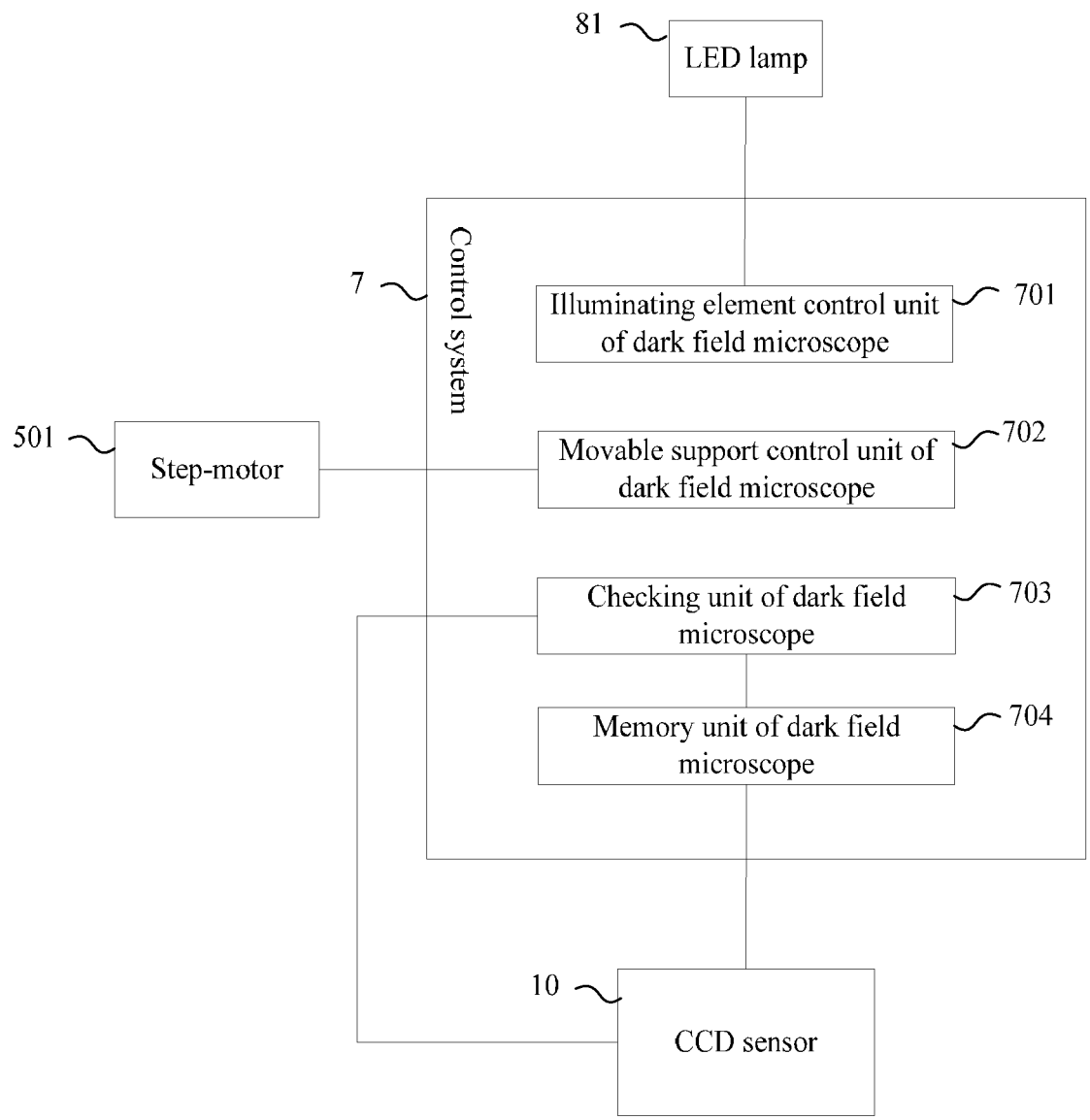

FIG. 17 shows a schematic diagram of a control system of a dark field microscope.

Figure 18:
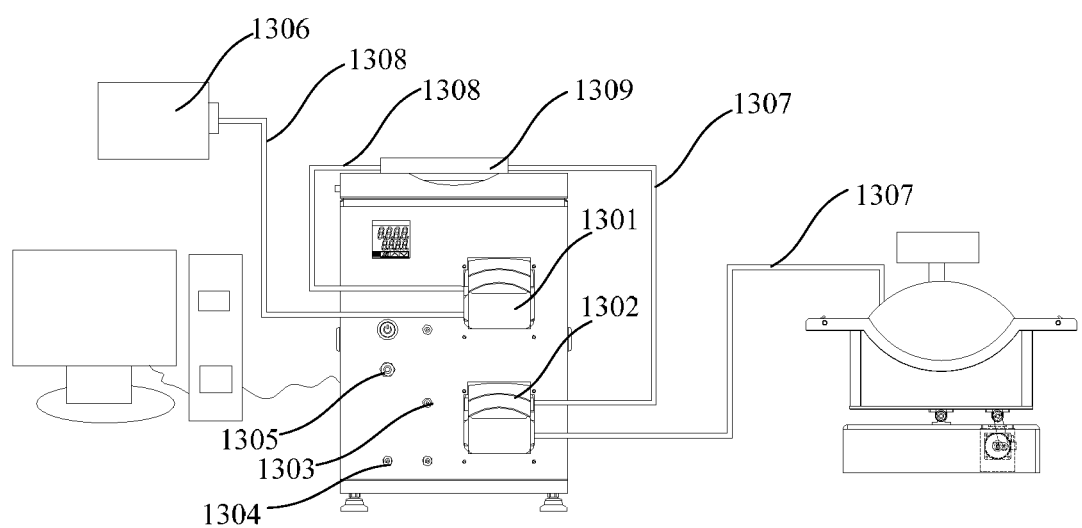

FIG. 18 shows a schematic diagram of a full-automatic cell culture system.

Figure 19:
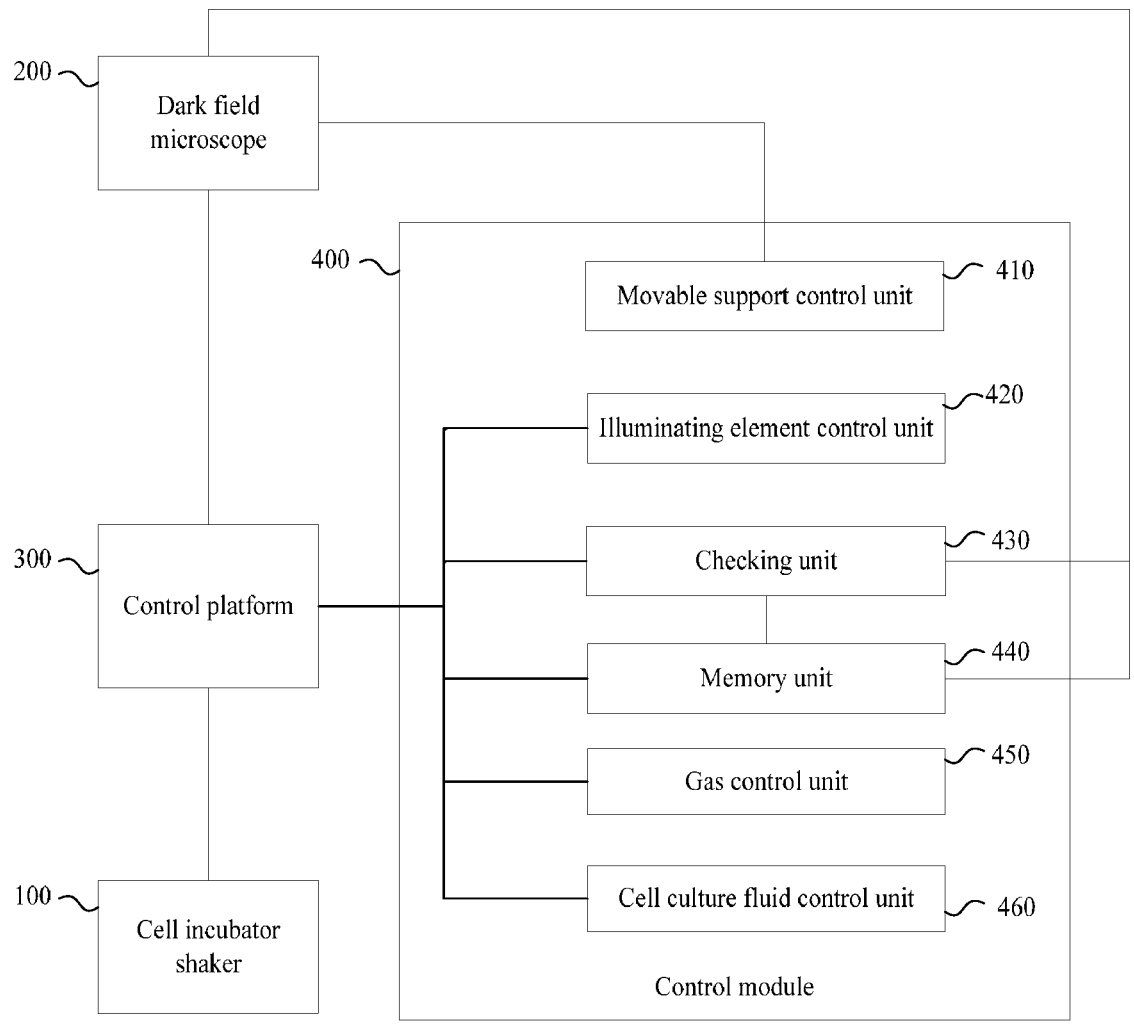

FIG. 19 shows a schematic diagram of a control module according to an embodiment of the present invention.

Figure 20:
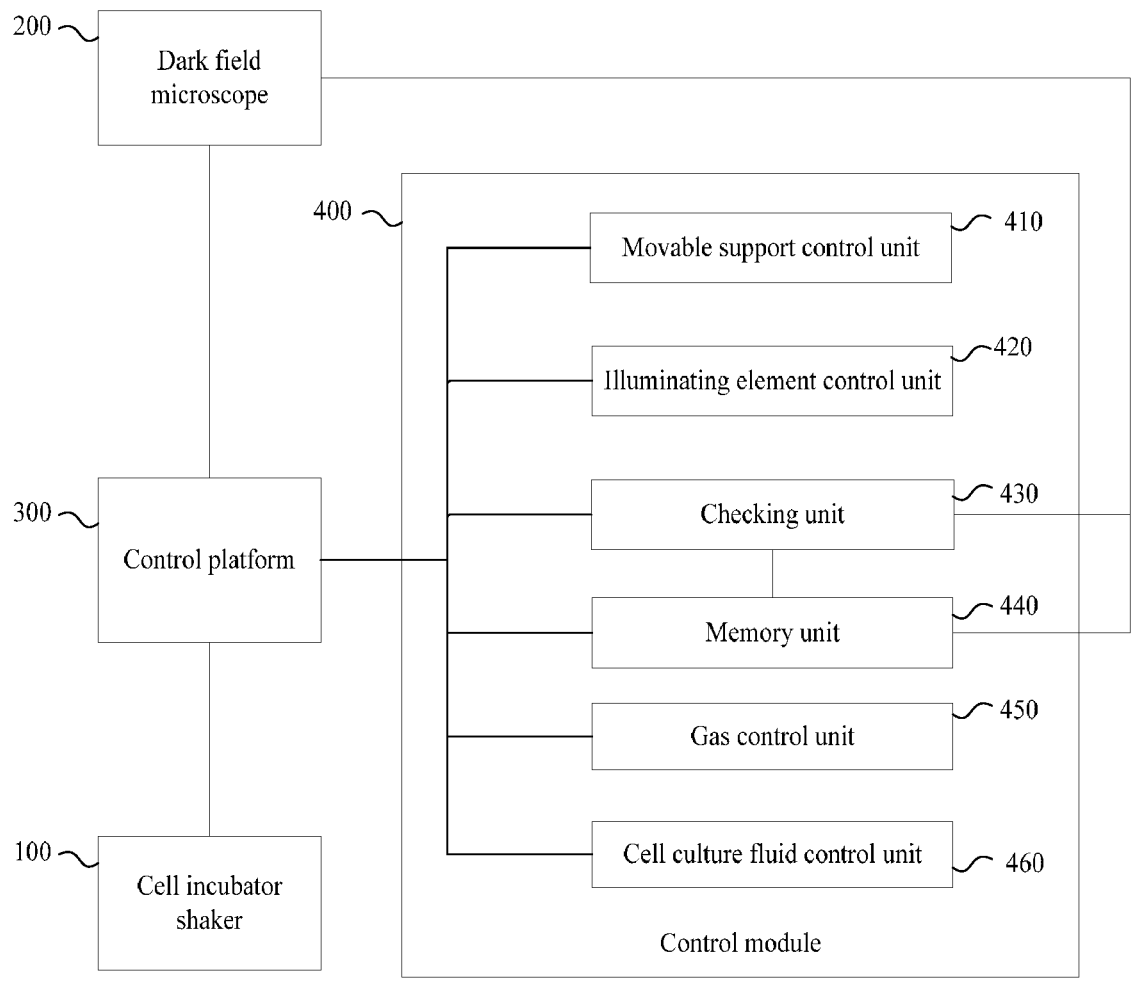

FIG. 20 shows a schematic diagram of a control module according to a second embodiment of the present invention.

Figure 21:
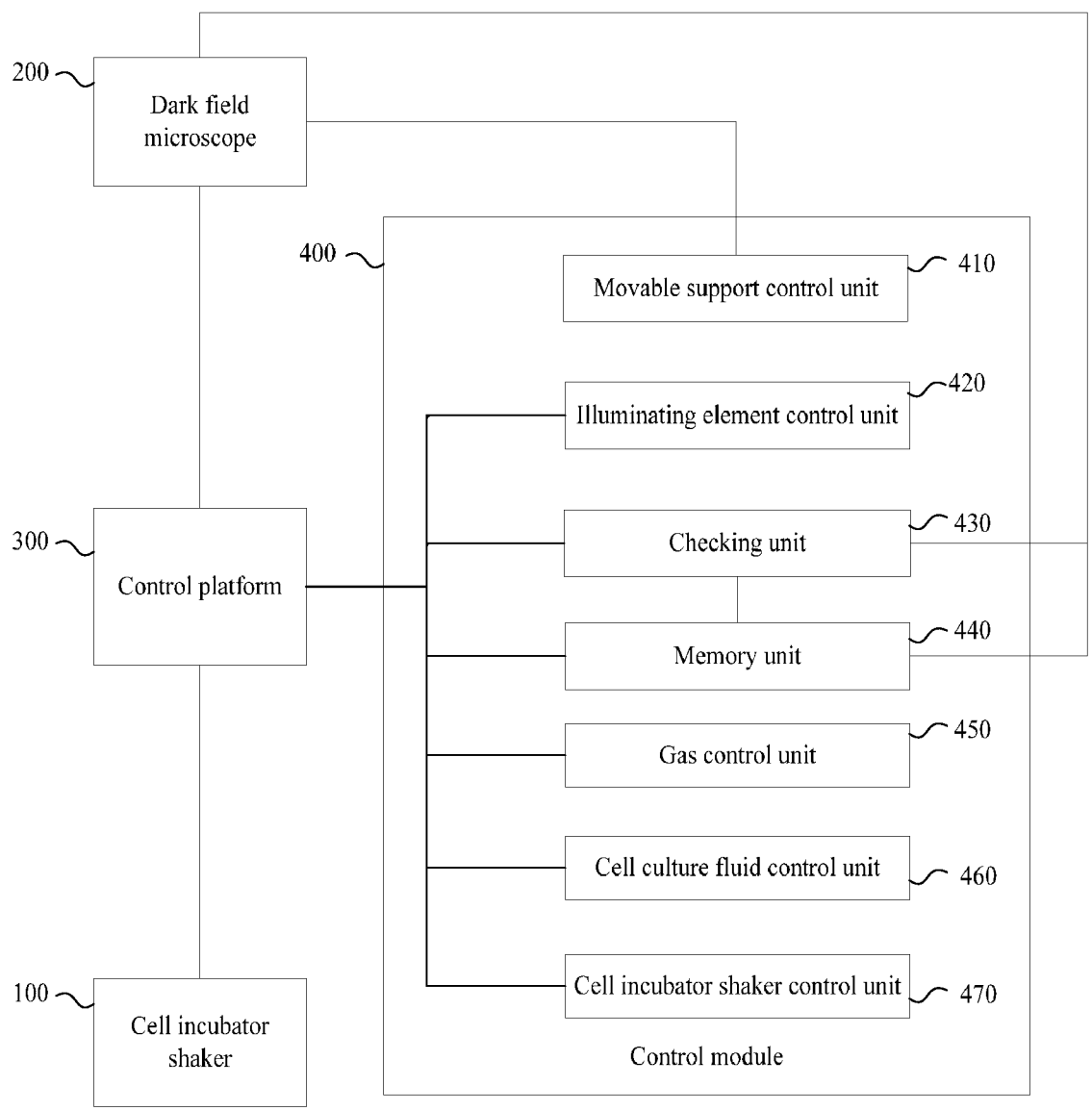

FIG. 21 shows a schematic diagram of a control module according to a third embodiment of the present invention.

Figure 22:
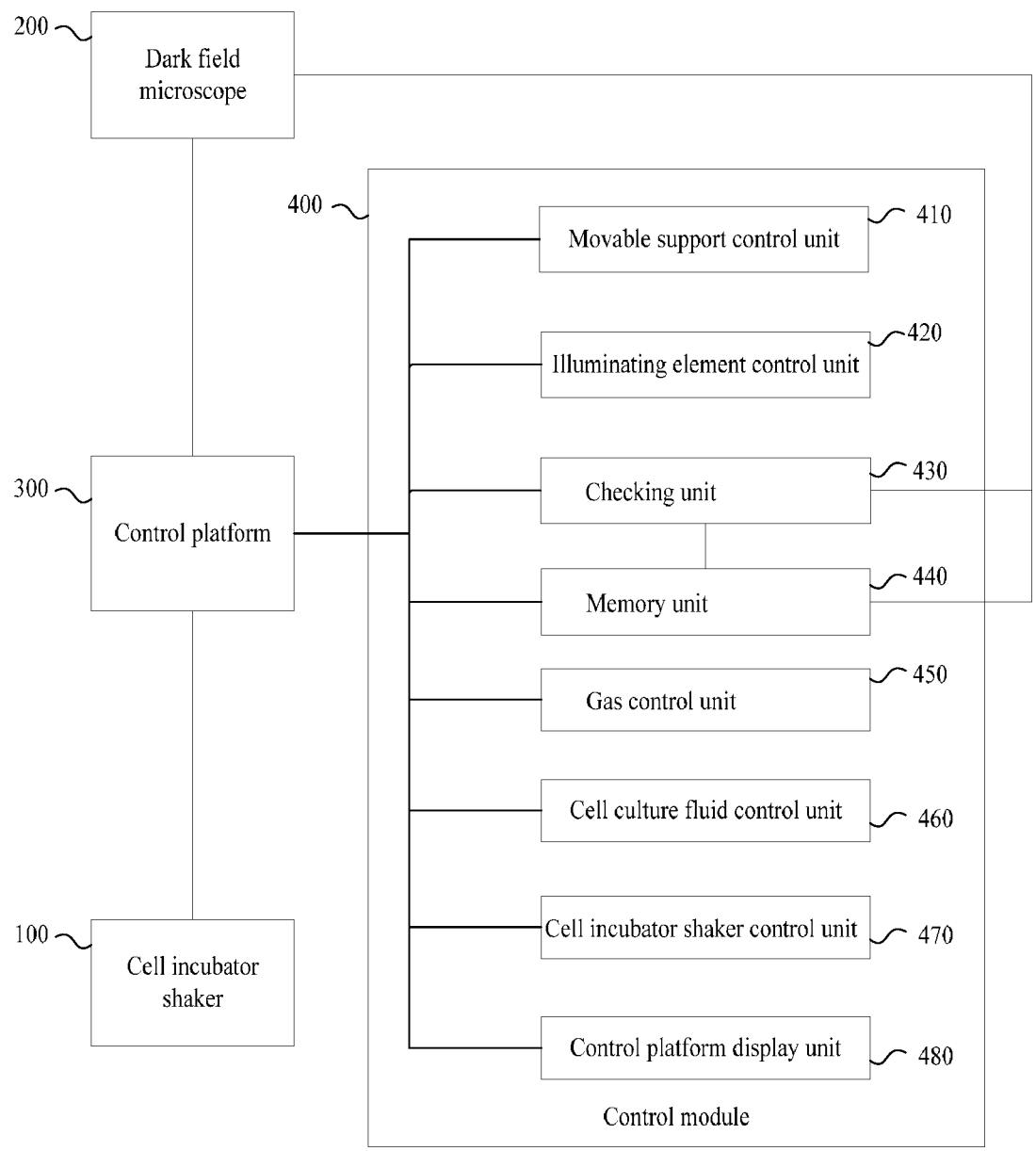

FIG. 22 shows a schematic diagram of a control module according to a fourth embodiment of the present invention.

1 Culture bag support frame
11 Arc-shaped bottom plate
111 Accessory fixing hole positions
112 Object lens inserting gap
113 Baffles
114 Heating plate
12 Cell culture bag fixing parts
121 Platforms
122 Fixing rod clamps
123 Fixing rod inserting mechanisms
124 Heightening supports
2 Swing frame
21 Swing base
211 Support arms
3 Shake device
31 Swing components
311 Hinge seat
312 Vertical reciprocating movement mechanism
32 Substrate
4 Cell culture bag
41 Closed bag body
411 External liquid adding port
412 External liquid injecting port
414 Gas inlet
413 Gas outlet
415 Liquid recycling port
4161 Upper bag piece
4162 Lower bag piece
4163 Left side bag piece
4164 Right side bag piece
417 Sensor connectors
4171 Sensor connector configured to connect with a pH value sensor probe
4172 Sensor connector configured to connect with a dissolved oxygen sensor probe
41701 Basal disc
41702 Cavity for containing sensor probe
41703 Transparent partition
41704 Internal threads
41795 Flange
418 Aseptic quick connectors
419 Transparent observation area
42 Fixing part
431 Silicone pipe
432 Luer connector
433 Tee
434 Needleless sampler
435 Air filter
436 Air cutoff valve
437 Film clip
438 Binding band
44 Sealing area
5 Support base
501 Step-motor
502 Slide block
503 Base
6 Pipe diameter unit
61 Object lens
7 Control system
701 Illuminating elements control unit of dark field microscope
702 Movable support control unit of dark field microscope
703 Checking unit of dark field microscope
704 Memory unit of dark field microscope
8 Lamp holder
81 LED lamps
82 Lens
83 Centermost light ray
9 Movable support
10 Photosensitive element (CCD sensor)
13 Control cabinet
1301 First peristaltic pump
1302 Second peristaltic pump
1303 pH detection connector
1304 Dissolved oxygen detection connector
1305 Gas outlet
1306 External cell culture fluid
1307 Second pipeline
1308 First pipeline
1309 Preheating bag
100 Cell incubator shaker
200 Dark field microscope
300 Control platform
400 Control module
410 Movable support control unit
420 Illuminating elements control unit
430 Checking unit
440 Memory unit
450 Gas control unit
460 Cell culture fluid control unit
470 Cell incubator shaker control unit
480 Control platform display unit

DETAILED DESCRIPTION OF THE PREFERRED EMBODIMENTS

The implementing modes of the present invention are explained with specific embodiments in the following, and those skilled in the art could easily understand other advantages and effects of the present invention by the content disclosed in the description.

With reference to FIGS. 1 to 22, the structures, proportions, sizes and the like as shown in the drawings of the present invention are merely intended to cooperatively explain the content disclosed in the present description rather than limiting implementable limiting conditions of the present invention, and therefore have no technically substantial significance. Any structural modification, any change of a proportional relation or any adjustment on the size should fall within the scope covered by the technical content disclosed by the present invention without affecting the effects generated and the purposes achieved by the present invention. Meanwhile, the terms such as "upper", "lower", "left", "right", "middle" and "one" referred in the present description are merely intended for clear description rather than limiting an implementing range of the present invention, and the change or adjustment of a relative relationship should be viewed in the implementing scope of the present invention without substantially changing the technical content.

Embodiment 1 Culture Bag Support Frame for Continuous Cell Incubator Shaker

Figure 1:
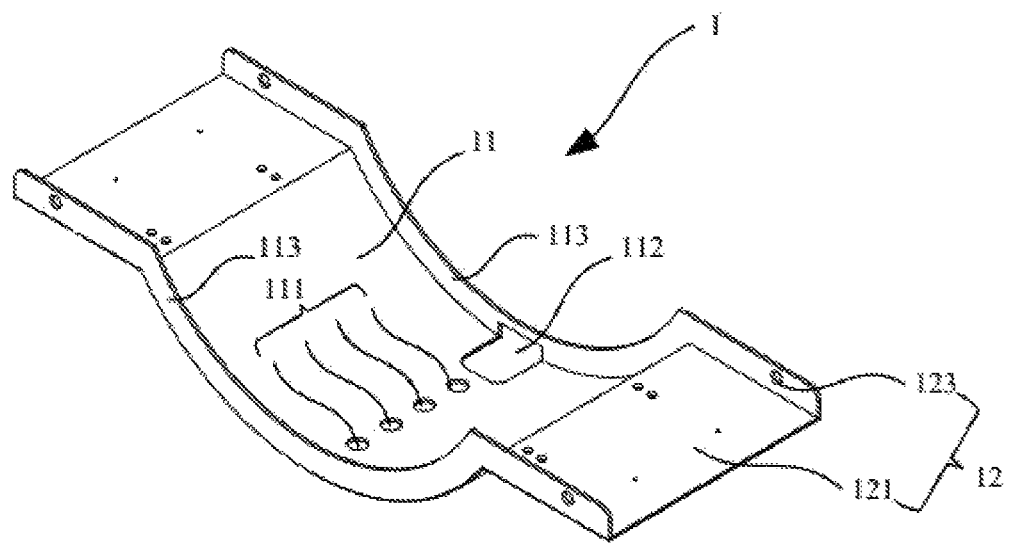
FIG. 1 shows a schematic diagram of a culture bag support frame according to an embodiment of the present invention.

The culture bag support frame 1 for a continuous cell incubator shaker as shown in FIG. 1 comprises an arc-shaped bottom plate 11 and cell bag fixing parts 12, and the arc-shaped bottom plate 11 is provided with one or more accessory fixing hole positions 111.

The arc-shaped bottom plate 11 is used for containing a main body of an arc-shaped 3D cell culture bag. Due to the design of the arc-shaped bottom plate, in the process of cell culture, the bottom of the arc-shaped 3D cell culture bag can keep arch-shaped. Therefore, in the process of cell culture, a shearing force generated by shaking of the culture platform is minimum; and the damage of the shearing force to the cells is also minimum.

Preferably, both sides of the arc-shaped bottom plate are arc-shaped.

Preferably, the accessory fixing hole positions 111 are provided with internal threads for better fixing an external accessory. The external accessory may be the probe of various detectors, such as pH value probe, and dissolved oxygen detection probe, etc. The external accessory may also be the accessories for cell continuous culture, such as various external liquid inlet pipes, external liquid injection parts, liquid outlet pipes, external gas delivery pipes, etc.

In a preferred embodiment, the arc-shaped bottom plate 11 is provided with an object lens inserting gap 112. In order to observe the cell condition in real time in continuous cell culture, a transparent observation area may be disposed on the bottom of the culture bag, and the object lens inserting gap 112 is matched with the transparent observation area and can be inserted by the object lens, thereby using the object lens to directly observe the cell condition in the cell bag.

The arc-shaped bottom plate is in a downward sunk arc shape under the use state. Further, the object lens inserting gap 112 is disposed in the sunk bottom area of the arc-shaped bottom plate. Further, the object lens inserting edge 112 is close to the edge of the arc-shaped bottom plate, for the object lens to enter and exit conveniently.

Further, in a preferred embodiment, the edge of the arc-shaped bottom plate 11 is provided with baffles 113. The baffles can prevent the cell culture bag from slipping off and shifting out from the culture bag support frame.

Figure 2:
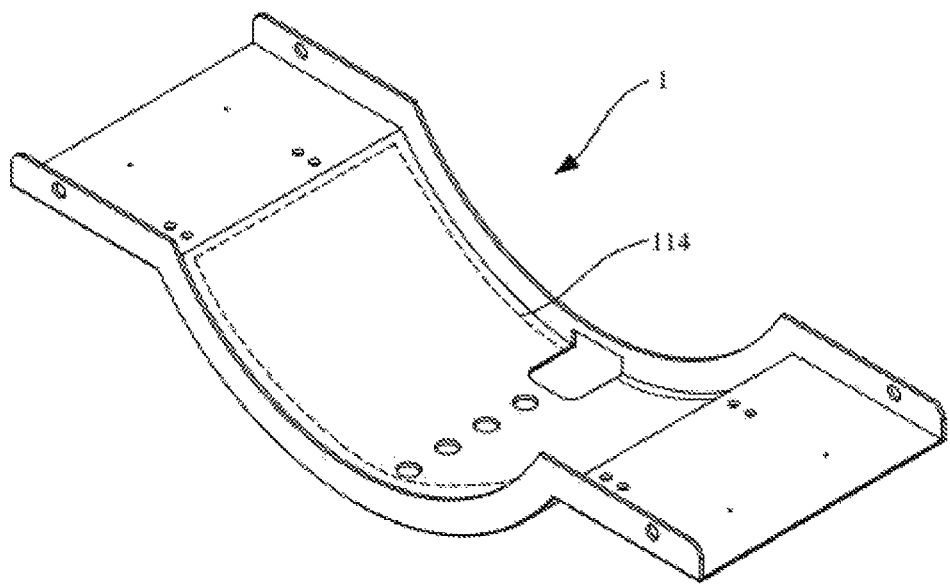
FIG. 2 shows a schematic diagram of a culture bag support frame according to a second embodiment of the present invention.

In the preferred embodiment as shown in FIG. 2, the arc-shaped bottom plate 11 is further provided with a heating plate 114. The heating plate is used to heat during cell culture to provide a proper temperature.

As shown in FIG. 1, the cell culture bag fixing parts 12 may be disposed on both sides of the arc-shaped bottom plate and may comprise platforms 121 extending from two sides of the arc-shaped bottom plate along a horizontal direction, and the platforms are provided with parts matched with the fixing parts on the cell bag. For example, the parts may be parts fixed by a mechanical force, an adhesive force, a magnetic force, etc. The cell bag with fixing rods is correspondingly disposed, and the parts matched with the fixing parts on the cell bag may be fixing rod clamps and/or fixing rod inserting mechanisms. In the preferred embodiment shown in FIG. 5, fixing rods are disposed on both sides of the cell bag, the platforms are provided with fixing rod clamps 122 and fixing rod inserting mechanisms 123, by combining the both, the connection with the fixing rod of the cell bag is detachable simply, the cell culture bag can be better fixed, and can be prevented from separating from the support frame due to shaking.

Figure 3:
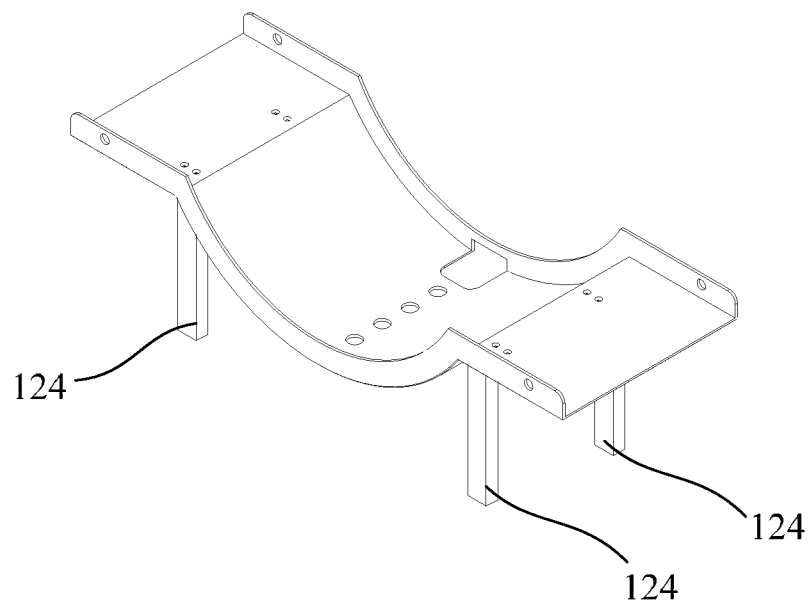
FIG. 3 shows a schematic diagram of a culture bag support frame according to a third embodiment of the present invention.

Further, as shown in FIG. 3, heightening supports 124 are further disposed on the lower part of the culture bag support frame for a continuous cell incubator shaker, to reserve an inserting space for the external accessory below the arc-shaped bottom plate. The heightening supports 124 may overhead the arc-shaped bottom plate, such that a clearance for mounting the external accessory is reserved below the accessory fixing hole positions 111 or the object lens inserting gap 112 of the arc-shaped bottom plate.

Figure 4:
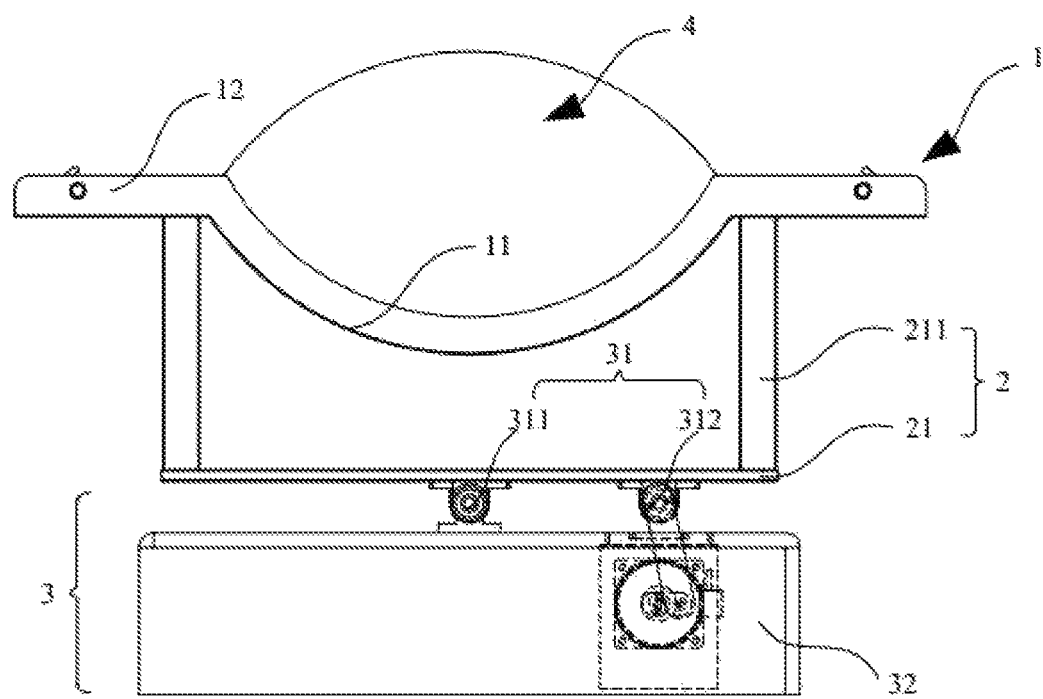
FIGS. 4, 5, and 6 show schematic diagrams of a cell incubator shaker according to an embodiment of the present invention.
Figure 5:
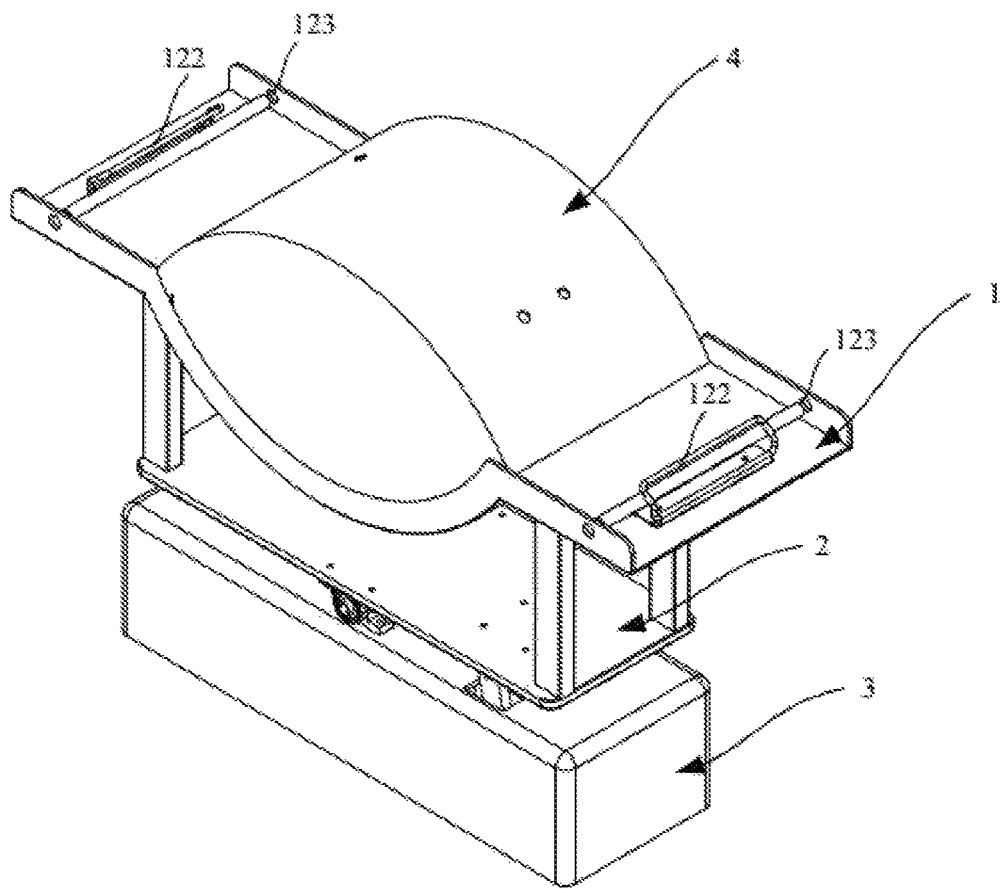
Figure 6:
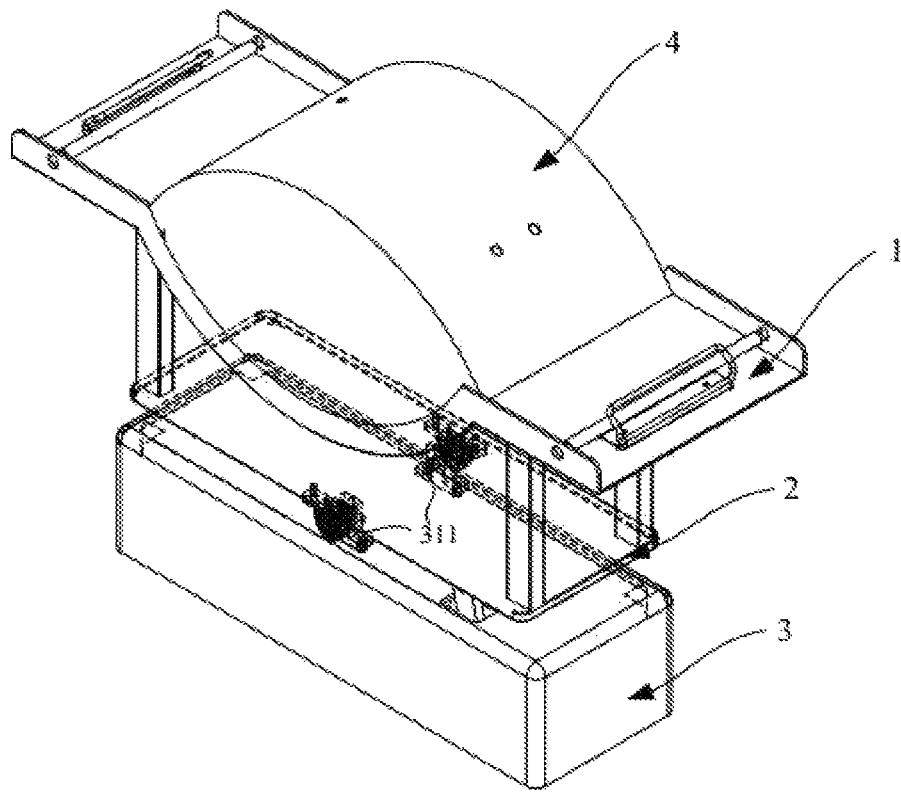

When in use, the culture bag support frame for a continuous cell incubator shaker according to the present invention is preferably used in the continuous cell incubator shaker as shown in FIGS. 4-6 and in combination with a three-dimensional cell culture bag 4. The continuous cell incubator shaker according to the present invention comprises a culture bag support frame 1, a swing frame 2 and a shake device 3, wherein the swing frame 2 comprises a swing base, when the support frame is not provided with the heightening supports 124, the swing base should be provided with support arms (equivalent to the heightening supports 124), and the culture bag support frame is fixed on the support arms. The shake device 3 is not limited to the drawings, and can be any mechanism capable of realizing a swing action.

When in work, under driving of a motor, the shake device 3 pushes the swing base 21 to perform swing motion, and further drives the culture bag support frame fixed on the support arms to drive the cell culture bag 4 to shake. The support frame heats the cell culture by the heating plate, and various monitoring probes can be connected on the cell culture bag by the accessory fixing hole positions 111 disposed in the bottom of the support frame, so as to detect a cell culture state. In the culture process, the shaking can also be stopped, and the object lens is inserted into the object lens inserting gap 112 of the support frame, to directly observe the cell condition in the transparent cell culture bag without sampling.

Embodiment 2 Continuous Cell Incubator Shaker

The continuous cell incubator shaker as shown in FIGS. 4-6 comprises a culture bag support frame 1, a swing frame 2 and a shake device 3, wherein the culture bag support frame 1 is provided with an arc-shaped bottom plate 11 and cell culture bag fixing parts 12, the swing frame 2 comprises a swing base 21, the swing base 21 is provided with support arms 211, the culture bag support frame 1 and the swing frame 2 are fixedly connected by the support arms 211, the shake device 3 comprises a substrate 32, the substrate is provided with swing components 31, and the swing base 21 is connected to the swing components 31.

The arc-shaped bottom plate 11 is used for containing a main body part of an arc-shaped 3D cell culture bag 4. Due to the design of the arc-shaped bottom plate, in the process of cell culture, the bottom of the arc-shaped 3D cell culture bag can keep arch-shaped. Therefore, in the process of cell culture, a shearing force generated by shaking of the culture platform is minimum, and the damage of the shearing force to the cells is also minimum.

Preferably, both sides of the arc-shaped bottom plate are arc-shaped.

Further, as shown in FIG. 1, the arc-shaped bottom plate 11 may be provided with one or more accessory fixing hole positions 111. Preferably, the accessory fixing hole positions 111 is provided with internal threads for better fixing an external accessory. The external accessory may be the probe of various detectors, such as pH value probe, and dissolved oxygen detection probe, etc. The external accessory may also be the accessories for cell continuous culture, such as various external liquid inlet pipes, external liquid injection parts, liquid outlet pipes, external gas delivery pipes, etc.

In a preferred embodiment as shown in FIG. 2, the arc-shaped bottom plate 11 is provided with an object lens inserting gap 112. In order to observe the cell condition in real time in continuous cell culture, a transparent observation area may be disposed on the bottom of the culture bag, and the object lens inserting gap 112 is matched with the transparent observation area and can be inserted by the object lens, thereby directly observing the cell condition in the cell bag.

The arc-shaped bottom plate is in a downward sunk arc shape under the use state. Further, the object lens inserting gap 112 is disposed in the sunk bottom area of the arc-shaped bottom plate.

Further, in the preferred embodiment as shown in FIG. 1, the edge of the arc-shaped bottom plate 11 is provided with baffles 113. The baffles can prevent the cell culture bag from slipping off and shifting out from the culture bag support frame.

In the preferred embodiment as shown in FIG. 2, the arc-shaped bottom plate 11 is further provided with a heating plate 114. The heating plate is used to heat during cell culture to provide a proper temperature.

As shown in FIG. 1, the cell culture bag fixing parts 12 may be disposed on both sides of the arc-shaped bottom plate and may comprise platforms 121 extending from two sides of the arc-shaped bottom plate along a horizontal direction, and the platform is provided with parts matched with the fixing parts on a cell bag. For example, the part may be a part fixed by a mechanical force, an adhesive force, a magnetic force, etc. In the embodiment shown in FIG. 5, fixing rods are disposed on both sides of the cell bag, at this point, the platform may be provided with a fixing rod clamp 122 and/or a fixing rod inserting mechanism 123, thereby realizing detachable connection with the fixing rod of the cell bag.

The design of the support arms 211 in the swing frame 2 can play a role of heightening the culture bag support frame 1. Spaces for mounting or inserting external accessories are reserved below the accessory fixing hole positions 111 of the culture bag support frame 1. In the swing frame, the support arms may be integrally formed with the swing base to serve as part of the swing base 21, or may be an individual part which is mounted on the swing base, or may be integrally formed with the culture bag support frame 1. In one aspect, the support arms may reserve a space for the connection between the cell culture bag and the external accessory; in the other aspect, since the culture bag support frame 1 is heightened, the culture bag support frame 1 can swing within a larger range by only providing a slight swing force for the swing base 21.

In the embodiments shown in FIGS. 4-6, the swing base 21 is a flat plate and is provided with support arms 211 on two ends, the culture bag support frame 1 makes no contact with the swing base 21, and a clearance is reserved therebetween for mounting or inserting the external accessory, including various probes and the object lens.

The swing components 31 may be any existing mechanism capable of realizing a swing action.

In the preferred embodiment shown in FIG. 4, the swing components 31 comprises hinging seats 311 and at least one vertical reciprocating movement mechanism 312, the hinging seats 311 are disposed on the substrate 32, the swing base 21 of the swing frame 2 is hinged to the hinging seats 311, to provide a swing center, and the vertical reciprocating movement mechanism 312 is connected to or abutted against the swing base 21, such that the vertical reciprocating movement mechanism 312 can push the swing base 21 to perform reciprocating swing motion around the swing center.

The hinging seats 311 may be one or more, and in the embodiment shown in FIG. 6, in the middle of the substrate 32, two hinging seats 311 are disposed symmetrically, such that the swing is more stable. Based on the work of the vertical reciprocating movement mechanism 312, the swing frame can perform a swing action left and right.

The vertical reciprocating movement mechanism 312 may be various existing mechanisms capable of realizing the reciprocating motion, for example, an electric push rod, a linear motor or a crankshaft connecting rod mechanism, etc. Specifically, the vertical reciprocating movement mechanism 312 may comprise a motor and cams, the cams are fixed on an output shaft of the motor, and the cams are directly abutted against the swing base 21 or abutted against or hinged to the swing base 21 by a push rod capable of performing vertical movement in a guide groove. The motor of the vertical reciprocating movement mechanism 312 may be disposed in the substrate 32.

One or more vertical reciprocating movement mechanisms 312 may be provided. In general cases, one vertical reciprocating movement mechanism 312 can satisfy the swing requirements. Based on such swing design, the swing amplitude and frequency of the shaker can be easily adjusted by adjusting a vertical reciprocating movement frequency of the vertical reciprocating movement mechanism or adjusting a distance between the vertical reciprocating movement mechanism and the hinging seats.

When in work, under driving of the motor, the vertical reciprocating movement mechanism 312 pushes the swing base 21 to perform swing motion around the hinging seats, and the culture bag support frame 1 fixed on the support arms 211 is driven to drive the cell culture bag 4 to shake. The support frame heats the cell culture by the heating plate, and various monitoring probes can be connected on the cell culture bag by the accessory fixing hole positions 111 disposed in the bottom of the support frame, so as to detect a cell culture state. In the culture process, the shaking may also be stopped, and the object lens is inserted into the object lens inserting gap 112 of the support frame, to directly observe the cell condition.

Embodiment 3 Non-Contact Sensor Connector

Figure 7:
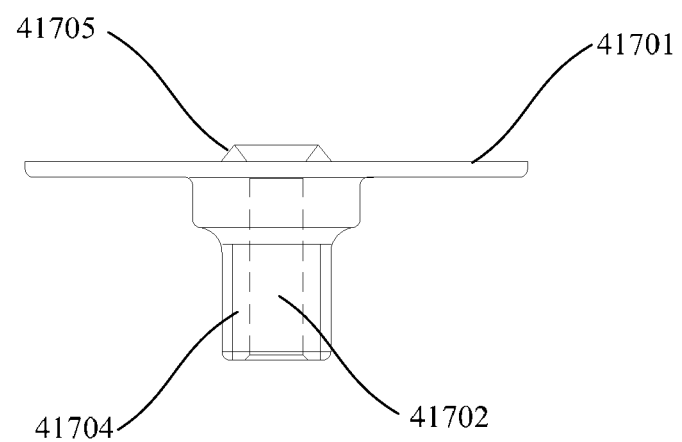
FIGS. 7, 8, and 9 show schematic diagrams of a sensor connector according to an embodiment of the present invention.
Figure 8:
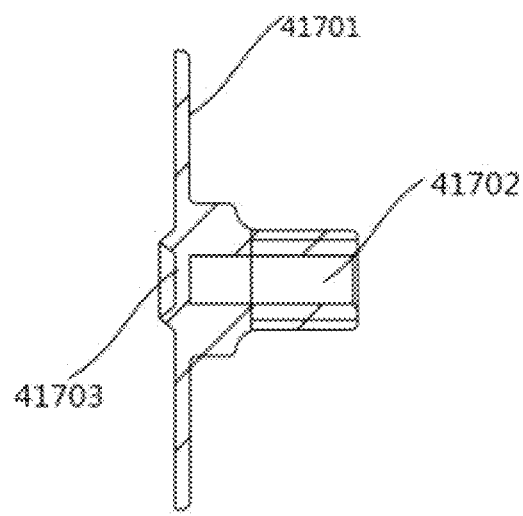
Figure 9:
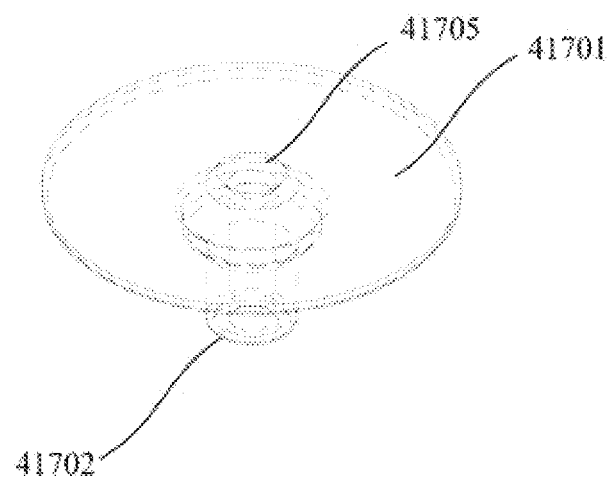

The non-contact sensor connector shown in FIGS. 7-9 comprises a basal disc 41701 and a cavity 41702 for containing sensor probe, wherein the basal disc 41701 is provided with a transparent partition 41703, the cavity 41702 for containing sensor probe and the basal disc 41701 are connected, and are located on one side of the transparent partition 41703, the other side of the transparent partition 41703 is provided with a converting film.

The open cavity for containing sensor probe refers to that the cavity is provided with an opening which can be conveniently inserted by a sensor probe.

The converting film and the cavity 41702 for containing sensor probe are respectively disposed on two sides of the transparent partition 41703. The arrow in FIG. 8 points to one side with the converting film. During working, the converting film makes contact with liquid to be tested, while the sensor probe is fixed in the cavity for containing sensor probe, opposite to the converting film, and separated from the liquid to be tested by the transparent partition.

The basal disc may be jointed with a mounting container for the liquid to be tested. By taking the cell culture bag as an example, one side surface or the edge of the basal disc 41701 is fused or welded with the cell culture bag, the position of the cell culture bag corresponding to the transparent partition 41703 is provided with an opening, the opening causes the converting film on the transparent partition to make contact with culture fluid in the cell culture bag, while the sensor probe inserted into the cavity 41702 for containing sensor probe is separated from the culture fluid in the cell culture bag due to the existence of the transparent partition 41703.

Preferably, the transparent partition 41703 is colorless and transparent, and both sides are smooth. The smooth transparent partition is more favorable for color transmission of the converting film.

The transparent partition 41703 is not limited to be only disposed in the middle of the basal disc 41701, as long as the basal disc of certain width is reserved around the transparent partition to be combined with the cell culture bag.

The cavity 41702 for containing sensor probe may be inserted with or in threaded connection with the sensor probe.

In a preferred embodiment, as shown in FIG. 7, internal threads 41704 are disposed in the cavity 41702 for containing sensor probe. Cooperatively, the sensor probe is provided with external threads. The threaded connection can further ensure the detection stability of the sensor probe.

The converting film is a pH-induced color change film or dissolved oxygen-induced color change film.

The pH-induced color change film can change a light transmission color according to the pH value of the liquid in contact. The pH-induced color change film may be obtained by film forming a mixture of a pH indicator and a film-forming material. The pH-induced color change film belongs to the prior art, for example, a pH sensing film used in a pH electrode.

The sensor probe with the converting film being the pH-induced color change film can be matched with an RGB sensor and a white light source. The detection principle for the pH value thereof is that: the pH-induced color change film changes the color according to the pH value of the liquid in contact therewith, so as to affect the color of the white light source transmitting through the film, the white light source cooperates with the pH-induced color change film to change a pH signal into a color signal, the RGB sensor detects the color signal transmitting through the converting film and the transparent partition, the pH value of the liquid to be tested in the mounting container for the liquid to be tested can be known according to a relationship between the colors of the converting film and the pH values, and the relationship between the colors of the converting film and the pH values can be obtained by detecting standard solutions with the known pH values in advance.

The dissolved oxygen-induced color change film can change a light transmission color according to the dissolved oxygen value of the liquid in contact. The dissolved oxygen-induced color change film may be obtained by film forming after a dissolved oxygen indicator and a film-forming material are mixed. The dissolved oxygen-induced color change film belongs to the prior art.

The sensor probe with the converting film being the dissolved oxygen-induced color change film can be matched with the RGB color sensor and the white light source. The principle for detecting the dissolved oxygen value is: the dissolved oxygen-induced color change film changes the color according to the dissolved oxygen concentration of the liquid in contact therewith, so as to affect the color of the white light source transmitting through the film, the white light source cooperates with the dissolved oxygen-induced color change film to change a dissolved oxygen signal into a color signal, the RGB color sensor detects the color signal transmitting through the converting film and the transparent partition, the dissolved oxygen value of the liquid to be tested in the mounting container for the liquid to be tested can be known according to a relationship between the colors and the dissolved oxygen concentrations, and the relationship between the colors of the converting film and the dissolved oxygen can be obtained by detecting standard solutions with the known dissolved oxygen concentrations in advance.

In order to better protect the converting film, a flange 41705 protruding out of the basal disc 41701 is disposed on the outer edge of the side surface of the transparent partition 41703 provided with the converting film. The flange can relieve the impact of the culture fluid on the converting film to further improve the detection stability of the sensor probe.

The cavity 41702 for containing sensor probe and the basal disc 41701 may be in fixed or detachable connection. The detachable connection manner comprises but not limited to insertion, threaded connection, etc.

Preferably, a joint between the cavity 41702 for containing sensor probe and the basal disc 41701 is in smooth transition.

The non-contact sensor connector according to present invention is particularly suitable for a cell culture bag.

By the non-contact sensor probe according to the present invention, the pH and the dissolved oxygen conditions of the liquid to be tested in the mounting container for the liquid to be tested can be converted into the color signals, by connecting the RGB sensor probes in the sensor probe containing cavity, the color signals can be converted into level signals or square wave signals, a controller for the RGB sensor reads the level signals or the square wave signals, and the pH value and the dissolved oxygen value of the culture fluid are obtained according to the converting relationship between the level signals corresponding to the colors of the converting film and the pH values and the dissolved oxygen. The converting relationship between the level signals corresponding to the colors of the converting film and the pH values and the dissolved oxygen can be obtained by a conventional technology, for example, by detecting the standard solutions with the known pH values or dissolved oxygen values in advance.

Embodiment 4 Cell Culture Bag

Figure 10:
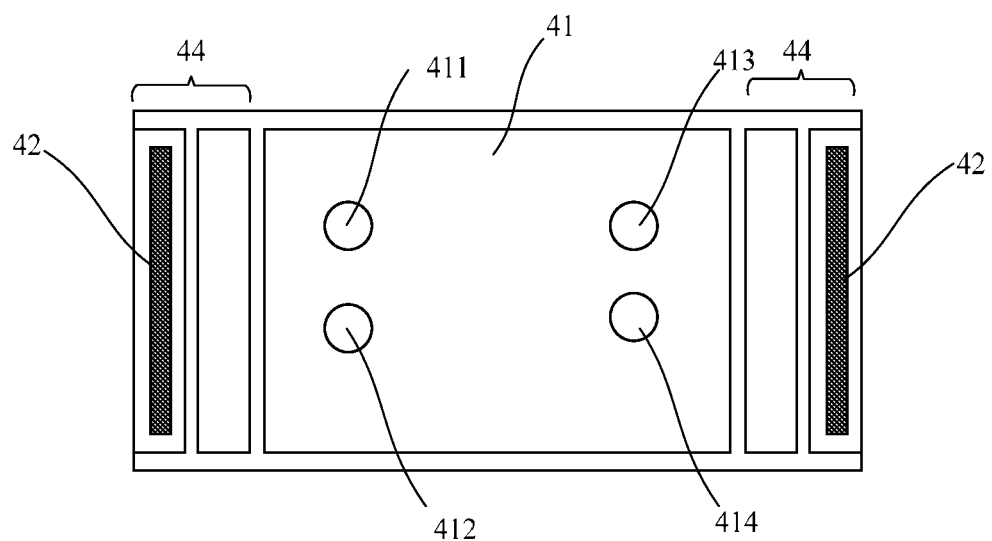
FIG. 10 shows a schematic diagram of the top surface of a cell culture bag according to an embodiment of the present invention.
Figure 11:
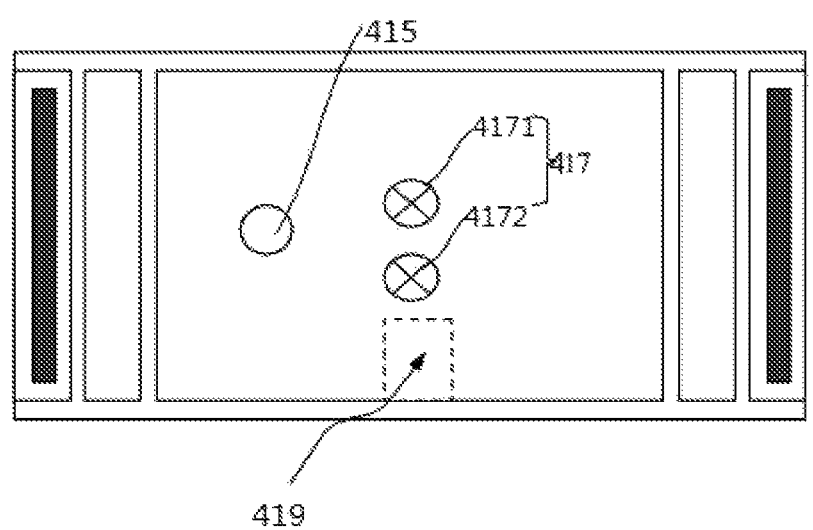
FIG. 11 shows a schematic diagram of the bottom surface of a cell culture bag according to an embodiment of the present invention.

The cell culture bag shown in FIGS. 10-11 comprises a closed bag body 41 and fixing parts 42 on two sides of the bag body, wherein the top surface of the closed bag body 41 is provided with an external liquid adding port 411, an external liquid injecting port 412, a gas inlet 414 and a gas outlet 413, the bottom surface of the closed bag body 41 is provided with a liquid recycling port 415 and at least one sensor connector 417, and the external liquid adding port 411, the external liquid injecting port 412, the gas inlet 414, the gas outlet 413, and the liquid recycling port 415 are all provided with aseptic quick connectors 418 (as shown in FIGS. 13 and 14).

The reason that the top surface of the cell culture bag is provided with the external liquid adding port, the external liquid injecting port, the gas inlet and the gas outlet is satisfying the requirement of adding the cell culture fluid and the external liquid (such as a penicillin solution, a streptomycin solution, and inoculated solution) and providing the gas content required by cell culture (for example, providing carbon dioxide) without moving out of the culture device in the process of cell culture. Part or all of the culture fluid can be replaced by the liquid recycling port in the bottom surface of the cell culture bag without moving out of the culture device. The bottom surface of the cell culture bag is provided with sensor connectors, which can be connected to a sensor to monitor related indexes in the cell culture fluid bag.

The quick connector refers to the connector which can realize connection or disconnection of a pipeline without tools. The adopted aseptic quick connectors are commercial aseptic quick connectors. The aseptic quick connectors can be fused or welded on the bag body.

The closed bag body may be made of a flexible material. The flexible material refers to a material which can be deformed after being stressed. Preferably, the material of the closed bag body is formed by compounding PE and EVOH.

In a preferred embodiment, materials of the closed bag body have a multilayer composite structure. Preferably, an innermost layer of the closed bag body is a polyethylene (PE) layer. The innermost layer is the layer in contact with the culture solution, and the stable PE material in contact with the culture fluid has low dissolved matter and no animal source.

In a more preferred embodiment, materials of the closed bag body have a five-layer composite structure which comprises the polyethylene (PE) layer, an adhesive layer, an ethylene vinyl alcohol layer layer, another adhesive layer and another PE layer from inside to outside in sequence. Materials of the five-layer composite structure can be purchased from the market.

The bag pieces forming the sealed bag body have a conventional thickness, which may be 0.325 mm in a preferred embodiment. The cell culture bag according to the present invention can be disinfected and sterilized with γ rays, and the irradiation dose is larger than or equal to 25 Gy and smaller than or equal to 50 Gy. The cell culture bag is sealed by heating.

Figure 12:
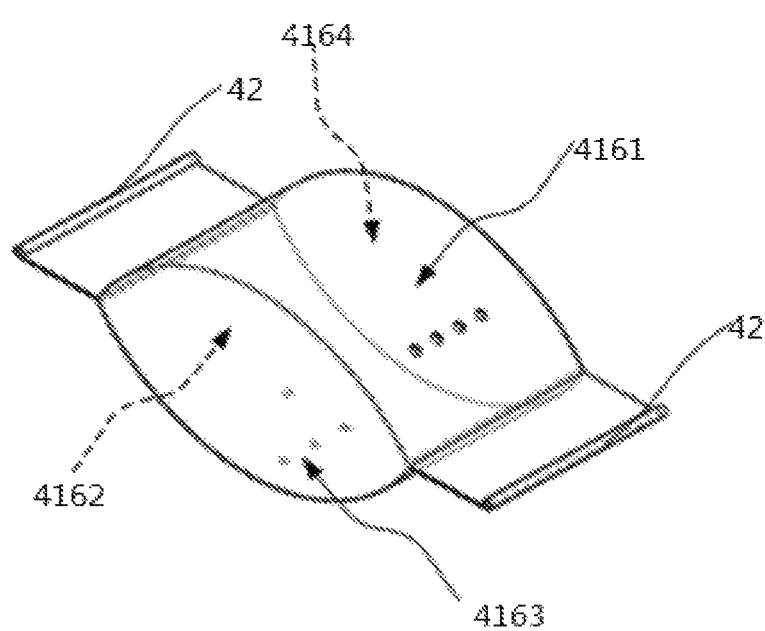
FIG. 12 shows a structural schematic diagram of a bag body of a cell culture bag according to a preferred embodiment of the present invention.

In a preferred embodiment shown in FIG. 12, the closed bag body forms a three-dimensional bag cavity by an upper bag piece 4161, a lower bag piece 4162, a left side bag piece 4163 and a right side bag piece 4164. More preferably, the lower bottom sides of the left side bag piece 4163 and the right side bag piece 4164 are arc-shaped. A shearing force generated when the culture platform is in shaking is small due to arc-shaped bottom sides of the cell culture bag, the damage of the shearing force to the cells is also reduced to the minimum. In the embodiment shown in FIG. 12, the left side bag piece 4163 and the right side bag piece 4164 are both oval, and the upper bag piece 4161 and the lower bag piece 4162 are rectangular.

In a preferred embodiment shown in FIG. 11, the middle of the bottom surface of the bag body 41 is further provided with a transparent observation area 419. The transparent observation area is disposed on the bottom of the cell culture bag, and a cell morphology observing device may be disposed on the culture platform to directly observe a cell condition in the cell culture bag from the bottom.

One or more sensor connectors may be disposed. Preferably, in the preferred embodiments as shown in FIGS. 11 and 14, two sensor connectors are disposed, wherein one sensor connector is a sensor connector 4171 configured to be connected to a pH value sensor probe, and the other sensor connector is the sensor connector 4172 configured to be connected with a DO sensor probe.

The sensor connector may be a non-contact sensor connector or a contact sensor connector. In preferred embodiments, the sensor connector is the non-contact sensor connector, i.e., after the sensor probe is inserted into the sensor connector, the probe makes no contact with the culture fluid in the bag body.

In a preferred embodiment, the non-contact sensor connector as shown in FIGS. 7-9 comprises a basal disc 41701 and a cavity 41702 containing sensor probe, the middle of the basal disc 41701 is provided with a transparent partition 41703, the cavity 41702 containing sensor probe and the basal disc 41701 are connected and are located on one side of the transparent partition 41703 and the other side (referring to the direction pointed by the arrow in the drawing) of the transparent partition 41703 is provided with a converting film. For the sensor connector connected to a pH value sensor probe, the converting film is a pH-induced color change film. The pH-induced color change film may be obtained by film forming after the pH indicator and the film-forming material are mixed. The pH-induced color change film belongs to the prior art, for example, a pH sensing film used by a pH electrode. For the sensor connector connected to a dissolved oxygen sensor probe, the converting film is a dissolved oxygen-induced color change film. The dissolved oxygen-induced color change film may be obtained by film forming after a dissolved oxygen indicator and a film-forming material are mixed. The dissolved oxygen-induced color change film belongs to the prior art.

By the sensor connectors, the pH and the dissolved oxygen conditions of the cell culture fluid in the cell culture bag can be converted into the color signals, and by connecting the RGB sensors in the sensor probes, the color signals can be read, so that the pH value and the dissolved oxygen values of the cell culture fluid are obtained according to the relationship between the colors of the converting film and the pH value and the dissolved oxygen.

The RGB color sensor matched with the non-contact sensor probe for use has no need of sterilization and disinfection and is not only more convenient to operate, but also can better prevent contamination.

The contact sensor connectors may be conventional aseptic quick connectors, and may be directly inserted or in threaded connection with the probe of a sterilized pH sensor or dissolved oxygen sensor. The foregoing non-contact sensor connector may also serve as the contact sensor connector after removing the transparent partition and the converting film.

The fixing parts 42 are configured to cooperatively fix the cell culture bag in the culture platform, the cell culture bag can be fixed by adopting various existing parts capable of fixing a liquid containing bag body, for example, the parts which can realize the fixing by single use, such as adhesive parts, or the parts required to be matched with a matching device disposed on the culture platform to play a role of fixing, for example, the parts fixed by a mechanical force, an adhesive force and a magnetic force, etc. In the embodiment as shown in FIG. 12, the fixing parts are fixing rods, the fixing rods may be detachably connected to fixing rod clamps or fixing rod inserting mechanisms additionally disposed on the culture platform, thereby achieving the purpose of fixing the cell culture bag.

Further, sealing areas 44 are disposed on both ends of the bag body 41, and the fixing rods are disposed in the sealing areas.

When in use, the cell culture bag according to the present invention can be fixed on the culture platform by the fixing parts 42, and the external liquid adding port 411, the external liquid injecting port 412, the gas inlet 413, the gas outlet 414, and the liquid recycling port 415 of the cell culture bag are respectively connected to a device providing external liquid and gas or a device recycling the liquid and gas by the aseptic quick connectors through pipelines, and the probes of corresponding sensors are inserted in the sensor connectors. In the process of cell culture, the external liquid can be added, the culture fluid can be replaced, a proper cell culture atmosphere can be provided and the condition of the cell culture fluid and the growth condition of the cells can be monitored according to needs anytime.

Specifically, the external liquid adding port 411 as shown in FIG. 13 may be quickly connected to an external pipeline by the aseptic quick connector 418, and further connected to an external liquid providing device, wherein the external pipeline may comprise a silicone pipe 431 and a Luer connector 432 in sequence, and further the silicone pipe may be connected to a tee 433 to be connected to multiple external liquid storage units.

The external liquid injecting port 412 as shown in FIG. 13 may be quickly connected to an external pipeline by the aseptic quick connector 418, and further connected to an external liquid providing device, wherein the external pipeline may comprise a silicone pipe 431, a Luer connector 432, and a needleless sampler 434 in sequence.

The gas inlet 414 as shown in FIG. 13 may be quickly connected to an external pipeline by the aseptic quick connector 418, and further connected to an external gas providing device, wherein the external pipeline may comprise a silicone pipe 431 and an air filter 435 in sequence.

The gas outlet 413 as shown in FIG. 13 may be quickly connected to an external pipeline by the aseptic quick connector 418, and further connected to the outside or a gas collecting device, wherein the external pipeline may comprise a silicone pipe 431, an air filter 435, a silicone pipe 431 and an air cutoff valve 436 in sequence.

The liquid recycling port 415 as shown in FIG. 14 may be quickly connected to an external pipeline by the aseptic quick connector 418, and further connected to an external liquid collecting device, wherein the external pipeline may comprise a silicone pipe 431 and a Luer connector 432 in sequence.

The silicone pipe of the pipeline may be provided with a film clip 437 to control the sample entrance and exit, and respective parts of the pipeline can be hermetically connected by a binding band 438.

The cell culture bag according to the present invention can meet the following cell culture requirements:

(1) The continuous culture condition does not need to change, the cell culture initial amount is small, with the increase of a cell density of the cell culture, the cell culture fluid needs to be increased continuously; and the cell culture bag according to the present invention can culture the cell within culture bag even a small initial cell culture amount.

(2) The temperature of cell culture: regardless of the initial amount of cell culture, the cell culture bag according to the present invention can be used for culture, and the cell culture bag can be subject to heating treatment.

(3) The pH and DO of the cell culture: due to the design of the 3D culture bag, a gas device necessary for cell culture can be connected, and the pH value and DO of the culture fluid can be revised by adjusting a gas environment.

(4) The non-contact pH and dissolved oxygen detection in the process of cell culture: by disposing a special nontoxic nonpoisonous photochemical material in the culture bag, the monitoring on the pH and DO of the culture fluid can be realized through the cell culture bag.

(5) The aseptic condition of cell culture: all interfaces, the culture fluid inlet, the interface of a recycling pipe and the gas inlet and outlet in the culture bag adopt an aseptic quick connecting manner, and the gas inlets and outlets are provided with the gas filters, thereby ensuring that the cell culture is in an aseptic state.

(6) In the case of shaking of the cell culture device, the shearing force applied to the cells in the culture bag is smaller, which is favorable for cell growth.

Embodiment 5 Dark Field Microscope for On-Line Observation of Cell Culture

The dark field microscope for on-line observation of cell culture as shown in FIG. 15 comprises but not limited to an illuminating element, a movable support 9, a support base 5, an object lens 61, a photosensitive element 10, a pipe diameter unit 6, an A/D converting unit, a control system and a power source module. The illuminating element is disposed on the top of the movable support 9, the movable support 9 is disposed on the support base 5, the pipe diameter unit 6 is connected on the lower part of the movable support 9, the object lens 61 is disposed on the pipe diameter unit 6 and is correspondingly disposed below the illuminating element, the photosensitive element 10 is disposed in the pipe diameter unit 6 and configured to collect a light source signal on the object lens 61, the A/D converting unit is connected to the photosensitive element 10, the control system is connected to the A/D converting unit, and the power source module is configured to provide electricity for the dark field microscope for on-line observation of cell culture.

In the present embodiment, the photosensitive element is a CCD sensor, and the A/D converting unit transmits an image signal obtained by the CCD sensor to the control system. The control system further comprises a checking unit provided in a computer, configured to check the content measured by the object lens under the current state, and a memory unit, configured to store the observed content needing to be stored.

In the present embodiment, the illuminating element is disposed on the top of the movable support 9, the illuminating element comprises but not limited to a round lamp holder 8, and a plurality of LED lamps disposed on the lamp holder 8 and surrounded as a plurality of concentric circles. The number of the concentric circles is preferably 5. The distance between the object lens to the lamp holder is 25 cm, and generally the distance may also be 10-30 cm, each concentric circle comprises ten to twenty LED lamps which provide light source for the whole device. The lamps on the circumference of each concentric circle can be turned on or off at the same time.

As shown in FIG. 16, the illuminating element further comprises a lens 82, and the lens is disposed below the LED lamps, such that the light rays emitted by the LED lamps are refracted after being transmitted through the lens, to meet the illuminating needs of the dark field. When the object lens is vertically upward, the included angle between the light rays emitted by the illuminating element and the horizontal plane is not larger than an angle A, and the angle A is the included angle between the centremost light ray 83 emitted by the illuminating element and a horizontal axis of the object lens 61. The object lens is configured to change a direction of the light rays. Preferably, most light rays emitted by the illuminating element are incident to the object lens after being refracted by the lens.

In a preferably embodiment, the support base 5, as shown in FIG. 15, comprises a step-motor 501, a slide mechanism and a base 503, the slide mechanism comprises a slide block 502 and a slide rail, the slide block 502 is connected on the base 503 by the slide rail, the step-motor 501 is connected to the control system and disposed on one end of the base 503, the slide block 502 is connected to the step-motor 501, and the movable support 9 is disposed on the slide block 502. Those ordinary skilled in the art know that the step-motor 501 can be implemented by a common step-motor on the market, and the step-motor 501 can drive the slide block 502 to move to change the relative position of the movable support 2 of the whole microscope.

In the present embodiment, the pipe diameter unit 6 is slidably connected on the movable support 9, a chute is provided at the position that the pipe diameter unit 6 is connected to the movable support 9, and the pipe diameter unit 6 can slide up and down along the chute, through holes are disposed in two opposite sides of the movable support 9, the two through holes are provided with screws respectively, when the pipe diameter unit 6 needs to be heightened, the screws can be loosened to move the pipe diameter unit 6, and the screws are screwed on when the pipe diameter unit 6 is adjusted to a proper position. Of course, the heightening and lowering adjustment is merely tiny adjustment, and a maximal adjusting range is 5 cm. Other known devices similar to a fastener on the market can also be adopted to play a role of fixing. A control system can also be used to control the LED lamps according to needs.

Referring to FIG. 17, in order to further optimize the design solution, the control system 7 comprises but not limited to a control unit 701 for the illuminating element of the dark field microscope; a control unit 702 for the movable support of the dark field microscope, for example, the user controls the step-motor to further control a moving distance of the movable support 2 by inputting specific values; a checking unit 703 of the dark field microscope, mainly configured for the user to check the content that can be observed by the object lens under the current state; and a memory unit 704 of the dark field microscope, mainly configured to store the observed content needing to be stored for the user for rechecking.

In another embodiment, the movable support 9 has a hollow structure, and the control unit for the illuminating element may be disposed in the hollow structure.

Those skilled in the art know that like the above process of controlling the illuminating element by the control system, the process of converting the image signal obtained by the CCD and the process of controlling the support base 5 to move can all be implemented by a computer, an integrated circuit module, a programmable logic device, other hardware or existing software in the prior art.

When observing the sample, particularly the cells cultured in the cell bag or a cell factory, the device according to the present disclosure has great advantages. When the sample is observed, the control system 7 can be used to move the movable support 9, such that the whole culture container is between the illuminating element and the object lens 61. When the observation is ended, the movable support 9 is moved off the culture container by the control system 7, and when the observation is required again, the position of the movable support 9 is moved by the control system.

Embodiment 6 Full-Automatic Cell Culture System

Referring to FIG. 18, the full-automatic cell culture system at least comprises: a control module, a control platform, a dark field microscope for on-line observation of cell culture, a cell incubator shaker, a cell culture bag and a power source module, wherein the control module is connected to the control platform, the control platform is respectively connected to and controls the cell incubator shaker and the dark field microscope for on-line observation of cell culture, and the dark field microscope for on-line observation of cell culture is configured to observe cells cultured on the cell incubator shaker, the cell culture bag is disposed on the cell incubator shaker and the power module supplies power for the whole system.

Cell Incubator Shaker

As shown in FIGS. 4-6, the cell incubator shaker in the full-automatic cell culture system comprises a culture bag support frame 1, a swing frame 2 and a shake device 3, wherein the culture bag support frame 1 is provided with an arc-shaped bottom plate 11 and cell culture bag fixing parts 12, the swing frame 2 comprises a swing base 21, the swing base 21 is provided with support arms 211, the culture bag support frame 1 and the swing frame 2 are fixedly connected by the support arms 211, the shake device 3 comprises a substrate 32, the substrate is provided with swing components 31, and the swing base 21 is connected to the swing components 31.

In a preferred embodiment as shown in FIG. 1, the arc-shaped bottom plate 11 is provided with an object lens inserting gap 112. In order to observe the cell condition in real time in continuous cell culture, a transparent observation area is disposed on the bottom of the culture bag, and the object lens inserting gap 112 is matched with the transparent observation area and can be inserted by the object lens, thereby directly observing the cell condition in the cell bag.

The arc-shaped bottom plate 11 is used for containing a main body part of an arc-shaped 3D cell culture bag. Due to the design of the arc-shaped bottom plate, in the process of cell culture, the bottom of arc-shaped 3D cell culture bag can keep arch-shaped. Therefore, in the process of cell culture, a shearing force generated by shaking of the culture platform is minimum, and the damage of the shearing force to the cells is also minimum.

Preferably, both sides of the arc-shaped bottom plate are arc-shaped.

Further, as shown in FIG. 1, the arc-shaped bottom plate 11 may be provided with one or more accessory fixing hole positions 111. Preferably, the accessory fixing hole positions 111 is provided with internal threads for better fixing an external accessory. The external accessory may be the probe of various detectors, such as pH value probe, and dissolved oxygen detection probe, etc. The external accessory may also be the accessories for cell continuous culture, such as various external liquid inlet pipes, external liquid injection parts, liquid outlet pipes, external gas delivery pipes, etc.

The arc-shaped bottom plate is in a downward sunk arc shape under the use state. Further, the object lens inserting gap 112 is disposed in the sunk bottom area of the arc-shaped bottom plate.

Further, in the preferred embodiment as shown in FIG. 1, the edge of the arc-shaped bottom plate 11 is provided with baffles 113. The baffles can prevent the cell culture bag from slipping off and shifting out from the culture bag support frame.

In the preferred embodiment as shown in FIG. 2, the arc-shaped bottom plate 11 is further provided with a heating plate 114. The heating plate is used to heat during cell culture to provide a proper temperature. The control module can set the temperature required by the cell culture bag 4, to control the heating of the heating plate.

As shown in FIG. 1, the cell culture bag fixing parts 12 may be disposed on both sides of the arc-shaped bottom plate and may comprise platforms 121 extending from two sides of the arc-shaped bottom plate along a horizontal direction, and the platform is provided with parts matched with the fixing parts on a cell bag. For example, the parts may be parts fixed by a mechanical force, an adhesive force, a magnetic force, etc., or the platform 121 is provided with screw holes and nuts to fix the cell culture bag 4 on the platform. In the embodiment as shown in FIG. 5, fixing rods are disposed on both sides of the cell culture bag 4, at this point, the platform may be provided with fixing rod clamps 122 and/or fixing rod inserting mechanisms 123, thereby realizing detachable connection with the fixing rod of the cell bag.

The design of the support arms 211 in the swing frame 2 can play a role of heightening the culture bag support frame 1. Spaces for mounting or inserting external accessories are reserved below the accessory fixing hole positions 111 of the culture bag support frame 1. In the swing frame, the support may be integrally formed with the swing base to serve as part of the swing base 21, or may be an individual part which is mounted on the swing base, or may be integrally formed with the culture bag support frame 1. In one aspect, the support arms may reserve a space for the connection between the cell culture bag and the external accessory; in the other aspect, since the culture bag support frame 1 is heightened, the culture bag support frame 1 can swing within a larger range by only providing a slight swing force for the swing base 21.

In the preferred embodiments as shown in FIGS. 4-6, the swing base 21 is a flat plate and is provided with support arms 211 on two ends, the culture bag support frame 1 makes no contact with the swing base 21, and a clearance is reserved therebetween for mounting or inserting the external accessory, including various probes and the object lens.

The swing components 31 may be any existing mechanism capable of realizing a swing action.

In the preferred embodiment as shown in FIG. 4, the swing components 31 comprise hinging seats 311 and at least one vertical reciprocating movement mechanism 312, the hinging seats 311 is disposed on the substrate 32, the swing base 21 of the swing frame 2 is hinged to the hinging seats 311, to provide a swing center, and the vertical reciprocating movement mechanism 312 is connected to or abutted against the swing base 21, such that the vertical reciprocating movement mechanism 312 can push the swing base 21 to perform reciprocating swing motion around the swing center.

The hinging seats 311 may be one or more, and in the embodiment as shown in FIG. 6, in the middle of the substrate 32, two hinging seats 32 are disposed symmetrically, such that the swing is more stable. Based on the work of the vertical reciprocating movement mechanism 312, the swing can perform a swing action left and right.

The vertical reciprocating movement mechanism 312 may be various existing mechanisms capable of realizing the reciprocating motion, for example, an electric push rod, a linear motor or a crankshaft connecting rod mechanism, etc. Specifically, the vertical reciprocating movement mechanism 312 may comprise a motor and cams, the cams are fixed on an output shaft of the motor, and the cams are directly abutted against the swing base 21 or abutted against or hinged to the swing base 21 by a push rod capable of performing vertical movement in a guide groove. The motor of the vertical reciprocating movement mechanism 312 may be disposed in the substrate 32.

One or more vertical reciprocating movement mechanisms 312 may be provided. In general cases, one vertical reciprocating movement mechanism 312 can satisfy the swing requirements. Based on such swing design, the swing amplitude and frequency of the shaker can be easily adjusted by adjusting a vertical reciprocating movement frequency of the vertical reciprocating movement mechanism or adjusting a distance between the vertical reciprocating movement mechanism and the hinging seats.

When in work, under driving of the motor, the vertical reciprocating movement mechanism 312 pushes the swing base 21 to perform swing motion around the hinging seats, and drives the culture bag support frame fixed on the support arms to drive the cell culture bag 4 to shake. The support frame heats the cell culture by the heating plate, and various monitoring probes can be connected on the cell culture bag by the accessory fixing hole positions 111 disposed in the bottom of the support frame, so as to detect a cell culture state. In the culture process, the shaking may also be stopped, and the object lens is inserted into the object lens inserting gap 112 of the support frame, to directly observe the cell condition.

Dark Field Microscope for On-Line Observation of Cell Culture

The dark field microscope for on-line observation of cell culture in the full-automatic cell culture system refers to FIG. 15 and comprises but not limited to an illuminating element a movable support 9, a support base 5, an object lens 61, a photosensitive element 10, a pipe diameter unit 6, and an A/D converting unit. The illuminating element is disposed on the top of the movable support 9, the movable support 9 is disposed on the support base 5, the pipe diameter unit 6 is connected on the lower part of the movable support 9, the object lens 61 is disposed on the pipe diameter unit 6 and is correspondingly disposed below the illuminating element, the photosensitive element 10 is disposed in the pipe diameter unit 6 and configured to collect a light source signal on the object lens 61, the A/D converting unit is connected to the photosensitive element 10 and the support base 5, and the control module is connected to the A/D converting unit.

In the present embodiment, the photosensitive element is a CCD sensor, and the A/D converting unit transmits an image signal obtained by the CCD sensor to the control system. The control system further comprises a checking unit provided in a computer, configured to check the content measured by the object lens under the current state, and a memory unit, configured to store the observed content needing to be stored.

In the present embodiment, the illuminating element is disposed on the top of the movable support 9, the illuminating element comprises but not limited to a round lamp holder 8, and a plurality of LED lamps disposed on the lamp holder 8 and surrounded as a plurality of concentric circles. The number of the concentric circles is preferably 5. The distance between the object lens to the lamp holder is 18 cm, and generally the distance may also be set to be 10-30 cm, each concentric circle comprises ten to twenty LED lamps which provide light source for the whole device. The lamps on the circumference of each concentric circle can be turned on or off at the same time.

As shown in FIG. 16, in order to meet the illumination of the dark field, when the object lens is vertically upward, the included angle between the light rays emitted by the illuminating element and the horizontal plane is not larger than an angle A, and the angle A is the included angle between the centre most light ray 83 emitted by the illuminating element and a horizontal axis of the object lens 61. The object lens is configured to change a direction of the light rays. Preferably, most light rays emitted by the illuminating element are incident to the object lens after being refracted by the lens.

In a preferably embodiment, the support base 5 comprises a step-motor 501, a slide mechanism and a base 503, the slide mechanism comprises a slide block 502 and a slide rail, the slide block 502 is connected on the base 503 by the slide rail, the step-motor 501 is connected to the control system and disposed on one end of the base 503, the slide block 502 is connected to the step-motor 501, and the movable support 2 is disposed on the slide block 502. Those ordinary skilled in the art know that the step-motor 501 can be implemented by a common step-motor on the market, and the step-motor 501 can drive the slide block 502 to move to change the relative position of the movable support 9 of the whole microscope.

In the present embodiment, the pipe diameter unit 6 is slidably connected on the movable support 9, a chute is provided at the position that the pipe diameter unit 6 is connected to the movable support 9, the pipe diameter unit 6 can slide up and down along the chute, through holes are disposed in two opposite sides of the movable support 9, the two through holes are provided with screws respectively, when the pipe diameter unit 6 needs to be heightened, the screws can be loosened to move the pipe diameter unit 6, and the screws are screwed on when the pipe diameter unit 6 is adjusted to a proper position. Of course, the heightening and lowering adjustment is merely tiny adjustment, and a maximal adjusting range is 5 cm. Other known devices similar to a fastener on the market can also be adopted to play a role of fixing. A control system can also be used to control the LED lamps according to needs.

In another embodiment, the movable support 9 has a hollow structure, and the control unit for the illuminating element may be disposed in the hollow structure.

When observing the sample, the device according to the present disclosure has great advantages. When the sample is observed, movement of the movable support 9 is controlled by the control module, such that the whole culture container is between the illuminating element and the object lens 61, the object lens 61 is used to observe the cells by the object lens inserting gap 112 of the cell incubator shaker, movement of the movable support 9 is controlled by the control module so as to leave from the culture container, and when the observation is required again, the control module is used to move the position of the movable support 9.

Cell Culture Bag

The cell culture bag adopted by the full-automatic cell culture system is as shown in FIGS. 10-11, the cell culture bag 4 comprises a closed bag body 41 and fixing parts 42 on two sides of the bag body, wherein the top surface of the closed bag body is provided with an external liquid adding port 411, an external liquid injecting port 412, a gas inlet 414 and a gas outlet 413, the bottom surface of the closed bag body 41 is provided with a liquid recycling port 415 and at least one sensor connector 417, and the external liquid adding port 411, the external liquid injecting port 412, the gas inlet 414, the gas outlet 413, and the liquid recycling port 415 are all provided with an aseptic quick connectors 418.

The reason that the top surface of the cell culture bag 4 is provided with the external liquid adding port, the external liquid injecting port, the gas inlet and the gas outlet is satisfying the requirement of adding the cell culture fluid and the external liquid (such as a penicillin solution, a streptomycin solution, and inoculated solution) and providing the gas content required by cell culture (for example, providing carbon dioxide) without moving out of the culture device in the process of cell culture. Part or all of the culture fluid can be replaced by the liquid recycling port in the bottom surface of the cell culture bag without moving out of the culture device. The bottom surface of the cell culture bag is provided with a sensor connector, which can be connected to a sensor to monitor related indexes in the cell culture fluid bag.

The quick connector refers to the connector which can realize connection or disconnection of a pipeline without tools. The adopted aseptic quick connectors are commercial aseptic quick connectors. The aseptic quick connectors can be fused or welded on the bag body.

The closed bag body may be made of a flexible material. The flexible material refers to a material which can be deformed after being stressed. Preferably, the material of the closed bag body is formed by compounding PE and EVOH.

In a preferred embodiment, materials of the closed bag body have a multilayer composite structure. Preferably, an innermost layer of the closed bag body is a PE layer. The innermost layer is the layer in contact with the culture solution, and the stable PE material in contact with the culture fluid has low dissolved matter and no animal source.

In a more preferred embodiment, materials of the closed bag body are of a five-layer composite structure which comprises the polyethylene (PE) layer, an adhesive layer, an Ethylene vinyl alcohol layer, another adhesive layer and another PE layer from inside to outside in sequence. Materials of the five-layer composite structure can be purchased from the market.

The bag pieces forming the sealed bag body have a conventional thickness, which is 0.325 mm in a preferred embodiment. The cell culture bag according to the present invention can be disinfected and sterilized with γ rays, and the irradiation dose is larger than or equal to 25 Gy and smaller than or equal to 50 Gy. The cell culture bag is sealed by heating.

In a preferred embodiment as shown in FIG. 12, the closed bag body forms a three-dimensional bag cavity by an upper bag piece 4161, a lower bag piece 4162, a left side bag piece 4163 and a right side bag piece 4164. More preferably, the lower bottom sides of the left side bag piece 4163 and the right side bag piece 4164 are arc-shaped. A shearing force generated when the culture platform is in shaking is small due to arc-shaped bottom sides of the cell culture bag, the damage of the shearing force to the cells is also reduced to the minimum. In the embodiment as shown in FIG. 12, the left side bag piece 4163 and the right side bag piece 4164 are both oval, and the upper bag piece 4161 and the lower bag piece 4162 are rectangular.

In a preferred embodiment as shown in FIG. 11, the middle of the bottom of the bag body 41 is further provided with a transparent observation area 419. The transparent observation area is disposed on the bottom of the cell culture bag, and a cell morphology observing device may be disposed on the culture platform to directly observe a cell condition in the cell culture bag from the bottom.

One or more sensor connectors may be disposed. Preferably, in the preferred embodiments as shown in FIGS. 11 and 14, two sensor connectors are disposed, wherein one sensor connector is a sensor connector 4171 configured to be connected to a pH value sensor probe, and the other sensor connectors are the sensor connectors 4172 configured to be connected with a DO sensor probe.

The sensor connectors may be non-contact sensors connector or contact sensor connectors. In preferred embodiments, the sensor connectors are the non-contact sensor connectors, i.e., after the sensor probe is inserted into the sensor connector, the probe makes no contact with the culture fluid in the bag body.

In the preferred embodiment as shown in FIG. 14, the non-contact sensor connector as shown in FIGS. 7-9 comprises a basal disc 41701 and a cavity 41702 containing sensor probe, the middle of the basal disc 41701 is provided with a transparent partition 41703, the cavity 41702 containing sensor probe and the basal disc 41701 are connected and are located on one side of the transparent partition 41703 and the other side (referring to the direction pointed by the arrow in the drawing) of the transparent partition 41703 is provided with a converting film. For the sensor connector connected to a pH value sensor probe, the converting film is a pH-induced color change film. The pH-induced color change film may be obtained by film forming after the pH indicator and the film-forming material are mixed. The pH-induced color change film belongs to the prior art, for example, a pH sensing film used by a pH electrode. For the sensor connector connected to a dissolved oxygen sensor probe, the converting film is a dissolved oxygen-induced color change film. The dissolved oxygen-induced color change film may be obtained by film forming after a dissolved oxygen indicator and a film-forming material are mixed. The dissolved oxygen-induced color change film belongs to the prior art.

By the sensor connectors, the pH and the dissolved oxygen conditions of the cell culture fluid in the cell culture bag can be converted into the color signals, and by connecting the RGB sensors in the sensor probes, the color signals can be read, so that the pH value and the dissolved oxygen values of the cell culture fluid are obtained according to the relationship between the colors of the converting film and the pH values and the dissolved oxygen. The pH and dissolved oxygen results obtained by the signals of the sensor connectors are both transmitted to the control module finally for recording and checking.

The RGB color sensor matched with the non-contact sensor probe for use has no need of sterilization and disinfection and is not only more convenient to operate, but also can better prevent contamination.

The contact sensor connector may be a conventional aseptic quick connector, and may be directly inserted or in threaded connection with the probe of a sterilized pH sensor or dissolved oxygen sensor. The foregoing non-contact sensor connector may also serve as the contact sensor connector after removing the transparent partition and the converting film.

The fixing parts 42 are configured to cooperatively fix the cell culture bag in the culture platform, the cell culture bag can be fixed by adopting various existing parts capable of fixing a liquid containing bag body, for example, the parts which can realize the fixing by single use, such as adhesive parts, or the parts required to be matched with a matching device disposed on the culture platform to play a role of fixing, for example, the parts fixed by a mechanical force, an adhesive force and a magnetic force, etc. In the embodiment as shown in FIG. 12, the fixing parts are fixing rods, the fixing rods may be detachably connected to fixing rod clamps or fixing rod inserting mechanisms additionally disposed on the culture platform, thereby achieving the purpose of fixing the cell culture bag.

Further, sealing areas 44 are disposed on both ends of the bag body 41, and the fixing rods are disposed in the sealing areas.

When in use, the cell culture bag according to the present invention can be fixed on the culture platform by the fixing parts 42, and the external liquid adding port 411, the external liquid injecting port 412, the gas inlet 414, the gas outlet 413, and the liquid recycling port 415 are respectively connected to a device providing external liquid and gas or a device recycling the liquid and gas by the aseptic quick connectors through pipelines, and the probes of corresponding sensors are inserted in the sensor connectors. In the process of cell culture, the external liquid can be added, the culture fluid can be replaced, a proper cell culture atmosphere can be provided and the condition of the cell culture fluid and the growth condition of the cells can be monitored according to needs anytime.

Specifically, the external liquid adding port 411 as shown in FIG. 13 may be quickly connected to an external pipeline by the aseptic quick connector 418, and further connected to an external liquid providing device, wherein the external pipeline may comprise a silicone pipe 431 and a Luer connector 432 in sequence, and further the silicone pipe may be connected to a tee 433 to be connected to multiple external liquid storage units.

The external liquid injecting port 412 as shown in FIG. 13 may be quickly connected to an external pipeline by the aseptic quick connector 418, and further connected to an external liquid providing device, wherein the external pipeline may comprise a silicone pipe 431, a Luer connector 432, and a needleless sampler 434 in sequence.

The gas inlet 414 as shown in FIG. 13 may be quickly connected to an external pipeline by the aseptic quick connector 418, and further connected to an external gas providing device, wherein the external pipeline may comprise a silicone pipe 431 and an air filter 435 in sequence.

The gas outlet 413 as shown in FIG. 13 may be quickly connected to an external pipeline by the aseptic quick connector 418, and further connected to the outside or a gas collecting device, wherein the external pipeline may comprise a silicone pipe 431, an air filter 435, a silicone pipe 431 and an air cutoff valve 436 in sequence.

The liquid recycling port 415 as shown in FIG. 14 may be quickly connected to an external pipeline by the aseptic quick connector 418, and further connected to an external liquid collecting device, wherein the external pipeline may comprise a silicone pipe 431 and a Luer connector 432 in sequence.

The silicone pipe of the pipeline may be provided with a film clip 437 to control the sample entrance and exit, and respective parts of the pipeline can be hermetically connected by a binding band 438.

The cell culture bag according to the present invention can meet the following cell culture requirements:

(1) The continuous culture condition does not need to change: the cell culture initial mount is small, with the increase of a cell density of the cell culture, the cell culture fluid needs to be increased continuously; and the cell culture bag according to the present invention can culture the cell within culture bag even a small initial cell culture amount.

(2) The temperature of cell culture: regardless of the initial amount of cell culture, the cell culture bag according to the present invention can be used for culture, and the cell culture bag can be subject to heating treatment.

(3) The pH and DO of the cell culture: due to the design of the 3D culture bag, a gas device necessary for cell culture can be connected, and the pH value and DO of the culture fluid can be revised by adjusting a gas environment.

(4) The non-contact pH and dissolved oxygen detection in the process of cell culture: by disposing a special nontoxic nonpoisonous photochemical material in the culture bag, the monitoring on the pH and DO of the culture fluid can be realized through the cell culture bag.

(5) The aseptic condition of cell culture: all interfaces, the culture fluid inlet, the interface of a recycling pipe and the gas inlet and outlet in the culture bag adopt an aseptic quick connecting manner, and the gas inlets and outlets are provided with the gas filters, thereby ensuring that the cell culture is in an aseptic state.

(6) In the case of shaking of the cell culture device, the shearing force applied to the cells in the culture bag is smaller, which is favorable for cell growth.

Control Platform

The control platform in the full-automatic cell culture system is provided with integrated circuit boards. The integrated circuit boards are at least connected to the dark field microscope and the cell incubator shaker respectively, and the integrated circuit boards are connected to the control module. The integrated circuit boards can control the dark field microscope and/or the illuminating element, and can control the frequency, the amplitude, and temperature of the cell incubator shaker.

Specifically, the integrated circuit boards are connected to the shake device of the cell incubator shaker, and can control a swing frequency and amplitude of the shaker. The integrated circuit boards are further connected to a temperature control heating element on the cell incubator shaker, and can control the temperature control heating element to heat the cell culture bag according to a preset temperature.

The control platform may also comprise a flow control element of a cell culture fluid pipeline for providing cell culture fluid for the cell culture bag, for example, a peristaltic pump. The integrated circuit boards are connected to the flow control element of the cell culture fluid pipeline, and can control the liquid flow of the cell culture fluid pipeline.

The control platform may also comprise a gas mixing unit providing gases for the cell culture bag. A gas flow element, such as a solenoid valve, suitable for controlling gas flow, is disposed in the gas mixing unit. The integrated circuit boards are further connected to the flow control element of the gas mixing unit, and can control the gas flow of a gas pipeline.

As a further improvement, the control platform may further comprise an automatic heating unit for preheating the cell culture fluid. The automatic heating unit comprises a heating element, for example, a preheating plate, a heating washer, a heating pipe, or a heating wire, etc. The automatic heating unit further comprises a temperature measuring element. The temperature measuring element may be disposed on the preheating plate and configured to sense the temperature of the preheating plate. The temperature measuring element may also adopt various common temperature measuring probes, sensors, etc. The automatic heating technology belongs to the prior art. Correspondingly, the integrated circuit boards are connected to the automatic heating unit and can control the automatic heating unit to preheat the cell culture fluid according to a preset temperature. The control platform may be provided with a preheating bag matched with the automatic heating unit, the preheating bag can be connected to the cell culture fluid pipeline and makes contact with the heating element of the automatic heating unit, thereby preheating the cell culture fluid.

The control platform may further comprise a pH detector and a dissolved oxygen detector. The pH detector and the dissolved oxygen detector are respectively connected to corresponding sensor connectors on the cell culture bag by a pH value sensor probe and a dissolved oxygen sensor probe. Correspondingly, the integrated circuit is connected to the pH detector and can control the pH detector to be ON or OFF; the integrated circuit boards are connected to the dissolved oxygen detector and can control the dissolved oxygen detector to be ON or OFF. The control platform may be further provided with a pH detection connector and a dissolved oxygen detection connector, which are configured to transmit the signals of a measured pH value and measured dissolved oxygen in the cell culture bag to the control module, respectively. In one aspect, the pH detection connector and the dissolved oxygen detection connector are respectively connected to corresponding sensor connectors on the cell culture bag by the pH sensor probe and the dissolved oxygen sensor probe, so as to transmit the information from the cell culture bag to the pH detector and the dissolved oxygen detector to obtain the pH and dissolved oxygen signals, in the other aspect, the pH detection connector and the dissolved oxygen detection connector are respectively connected to the control module to transmit the pH and dissolved oxygen signals to the control module.

The control platform may further comprise a display screen. Correspondingly, the integrated circuit boards are connected to the display screen and controls the display screen to be ON or OFF. The display screen may be further connected to the control module. The display screen may be configured to display setting parameters or system instant parameters needing to be known, which are selected from but not limited to: culture fluid temperature, culture time, a shaker speed, a swing amplitude, a gas proportion, the dissolved oxygen value, the pH value, etc.

In the embodiment as shown in FIG. 18, the control platform further comprises a control cabinet 13; an automatic heating unit, a preheating bag 1309 and peristaltic pumps are disposed on the control cabinet 13; the automatic heating unit comprises a preheating plate, the preheating bag 1309 is disposed on the preheating plate, the peristaltic pumps comprise a first peristaltic pump 1301 and a second peristaltic pump 1302, an inlet of the preheating bag 1309 is communicated with external cell culture fluid 1306 by a first pipeline 1308, an outlet of the preheating bag 1309 is communicated with the cell culture bag by a second pipeline 1307, the first peristaltic pump 1301 is connected to the first pipeline 1308, the second peristaltic pump 1302 is connected to the second pipeline 1307, and the automatic heating unit, the first peristaltic pump 1301 and the second peristaltic pump 1302 are connected to the control module. The first peristaltic pump 1301 and the second peristaltic pump 1302 can be connected to the control module by the integrated circuit boards so as to control the peristaltic pumps to add the cell culture fluid according to a flow rate set by the control module.

The control cabinet 13 is a carrier, there are no particular requirements on its shape, and a regular cubic structure is shown in the drawing, and various working units and the integrated circuit are provided therein. The preheating plate is disposed on the top of the control cabinet 13, and is provided with the preheating bag 1309 thereon. The preheating plate plays a role of heating the cell culture fluid in the preheating bag 1309. The cell culture fluid adopts the proper models sold on the market and suitable for cell culture. The volume of the preheating bag 1309 is 500 ml generally, which may be changed according to design or culture scale requirements.

The automatic heating unit may be connected to the control module. The control module may be connected to the automatic heating unit by the integrated circuit boards, so as to control the automatic heating unit according to the temperature set by the control module. The control module sets a preset temperature, when the temperature of the cell culture liquid in the preheating bag 1309 is lower than this temperature, the preheating plate will automatically heat the preheating bag 1309, and the heating is stopped when the temperature is reached.

The first peristaltic pump 1301 pumps the external cell culture fluid into the preheating bag 1309, the cell culture fluid is pumped into the cell culture bag by the second peristaltic pump 1302 when reaching a preset temperature.

Further, a gas mixing unit is further disposed in the control cabinet 13, the gas mixing unit is disposed on the gas pipeline, and the gas mixing unit is connected to an external gas source, which is mainly oxygen, air and carbon dioxide. The external gas enters the gas mixing unit and is mixed, then enters the cell culture bag after passing by the gas outlet 1305 and flowing by a third pipeline (not shown).

The gas mixing unit comprises a plurality of gas inlets and a mixed gas outlet pipe. More preferably, the gas inlets are not less than three, and at least can deliver the oxygen, the air and the carbon dioxide respectively. Each gas inlet may be provided with a gas flow control element. The elements capable of controlling the gas flow in the prior art can all be used for the gas inlets, for example, the switches and valves capable of realizing the adjustment on the gas flow, such as the solenoid valves. The gas mixing unit may further comprise a gas mixing cavity, and the gas inlets are led to the gas mixing cavity and then the gases are output by the mixed gas outlet pipe. Or the gas inlets are directly connected to the mixed gas outlet pipe and the gases are naturally mixed in the mixed gas outlet pipe.

The gas mixing unit is connected to the control module, and the gas supply, for example, the gas flow, the delivery time, the component proportions of various gases and the like, is set by the control module. The control module may be connected to the flow control element of the gas mixing unit by the integrated circuit boards, so as to control the gas delivery according to the gas mixing proportion, the gas flow, the delivery time and the like set by the control module.

Further, the control cabinet is further provided with a pH detector and a dissolved oxygen detector. The pH detector and the dissolved oxygen detector are connected to the sensor connectors on the control module and the cell culture bag to transmit the signals of the measured pH value and the measured dissolved oxygen in the cell culture bag to the control module. Specifically, the control cabinet is provided with the pH value detection connector 1303 and the dissolved oxygen connector 1304, and the pH detector and the dissolved oxygen detector are respectively connected to the corresponding sensor connectors on the cell culture bag and the control module by the connectors. Further, the pH detection connector and the dissolved oxygen detection connector are respectively connected to the corresponding sensor connectors on the cell culture bag by a pH value sensor probe and a dissolved oxygen sensor probe. The pH value detection connector 1303 and the dissolved oxygen detection connector 1304 can transmit the signals from the pH value sensor probe and the dissolved oxygen sensor probe to the pH detector and the dissolved oxygen detector by signal transduction parts (not shown). The pH value detection connector 1303 and the dissolved oxygen detection connector 1304 can also transmit the information of the pH value and the dissolved oxygen obtained by the pH detector and the dissolved oxygen detector to the control module. Cooperatively, the integrated circuit boards are connected to the pH detector and the dissolved oxygen detector, and can control the pH detector and the dissolved oxygen detector to be ON or OFF. The pH detection connector 1303 and the dissolved oxygen detection connector 1304 both adopt common signal transmission connectors on the market, for example, an SMA905 plug. The signal transduction parts adopt for example common optical fiber connecting lines on the market.

Control Module

Referring to FIGS. 19-22, the control module in the full-automatic cell culture system is shown, the control module 400 is connected to a control platform 300.

The user can control the system and check and record various parameters in cell culture and cell structures, etc., by the control module 400. Preferably, the control module may be disposed on a computer.

The control module 400 comprises but not limited to:

a movable support control unit 410, configured to control the movement of the movable support of the dark field microscope 200, wherein the movable support control unit is connected to a motor of the movable support, for example, the user controls the step-motor by inputting a specific value to further control a moving distance of the movable support 9; the movable support control unit may be directly connected to the motor of the movable support (as shown in FIG. 19), or the motor of the movable support may also be connected to the movable support control unit by integrated circuit boards of the control platform (as shown in FIG. 20);

an illuminating element control unit 420, configured to control an illuminating element of the dark field microscope 200, wherein the illuminating element control unit at least sets control parameters of the illuminating element, such as ON or OFF, brightness, time duration of the ON or OFF, etc. In a preferred embodiment, the integrated circuit boards of the control platform can control the illuminating element of the dark field microscope, and at this point, the illuminating element control unit is connected to the illuminating element of the dark field microscope by the integrated circuit boards of the control platform;

a checking unit 430, mainly configured to check the content that can observed by the object lens of the dark field microscope 200 under a current state, and/or parameters of a cell growth environment, for example, a pH value and a dissolved oxygen value. The memory unit is in signal connection with the dark field microscope, the pH detector and the dissolved oxygen detector;

a memory unit 450, mainly configured to store the content observed by the dark field microscope and environmental parameters in the cell growth process such as the pH value and dissolved oxygen, which need to be stored according to the consideration of the user, for rechecking, and the checking unit is in signal connection with the dark field microscope, the pH detector and the dissolved oxygen detector;

a gas control unit 460, mainly configured to control the gas mixing unit, wherein the gas control unit at least can set one or more of a gas mixing proportion, flow, and delivery time. The gas control unit can be connected to a flow control element of the gas mixing unit by the integrated circuit boards of the control platform, so as to set and control gas delivery, therefore, when the cell culture bag needs gas exchange, the external gases are input to the cell culture bag after being mixed by the set proportion; and a cell culture fluid control unit 460, mainly configured to control the automatic heating unit to heat the external cell culture fluid when the cell culture fluid in the cell culture bag needs to be replaced and control the cell culture fluid to be input into the cell culture bag. The culture fluid control unit at least can set a heating temperature of the automatic heating unit and a delivery speed of the cell culture fluid. The culture fluid control unit is connected to the control platform, and the culture fluid control unit can be connected to the automatic heating unit and the peristaltic pumps by the integrated circuit boards of the control platform, so that the cell culture fluid is input into the cell culture bag after being heated to a set temperature.

Further, as shown in FIGS. 21 and 22, the control module further comprises one or more of the following:

a cell incubator shaker control unit 470, configured to set a frequency and a swing amplitude of the cell incubator shaker 100 and a heating temperature for the cell culture fluid, wherein the cell shaker control unit is connected to the cell shaker, more preferably, the cell shaker control unit may be connected to the cell shaker by the integrated circuit boards of the control platform, such that the cell shaker can work according to the set frequency, swing amplitude and temperature; and a control platform display unit 480, connected to a display screen of the control platform to set displayed content.

Those skilled in the art know that, as mentioned above, the process of controlling the movable support by the above control module, the process of controlling the illuminating element, the process of checking the content of the cell culture bag and various parameter, the process of controlling the external gas source and the cell culture fluid to enter the cell culture bag, and the process of controlling the cell incubator shaker can all be implemented by a computer, an integrated circuit module, a programmable logic device, other hardware or existing software in the prior art.

The above embodiments merely illustratively explain the principle and effects of the present invention rather than limiting the present invention. Any skilled familiar with the art can modify or change the above embodiments without disobeying the spirit and scope of the present invention. Therefore, all equivalent modifications or changes made by those skilled with common knowledge in the art without departing from the spirit and technical thought disclosed in the present invention should still be covered by claims of the present invention.

What is claimed is:

1. A full-automatic cell culture system, characterized by at least comprising: a control module, a control platform, a dark field microscope for on-line observation of cell culture, a cell incubator shaker, a cell culture bag and a power source module; wherein the cell incubator shaker comprises a culture bag support frame, a swing frame and a shake device, the culture bag support frame is provided with an arc-shaped bottom plate and cell culture bag fixing parts, the swing frame comprises a swing base, the swing base is provided with support arms, the culture bag support frame and the swing frame are fixedly connected by the support arms, the shake device comprises a substrate, the substrate is provided with swing components, the swing base is connected to the swing components, and the arc-shaped bottom plate is provided with an object lens inserting gap;

the cell culture bag comprises a closed bag body, and the middle of the bottom surface of the bag body is provided with a transparent observation area; and the bag body is disposed on the cell incubator shaker, and the transparent observation area is matched with the object lens inserting gap;

the dark field microscope for on-line observation of cell culture comprises an object lens, illuminating elements, a movable support, a support base, a photosensitive element, a pipe diameter unit, and an A/D converting unit, wherein the object lens is able to be inserted into the object lens inserting gap in the cell incubator shaker, the illuminating elements are disposed on the top of the movable support, the movable support is disposed on the support base, the pipe diameter unit is connected on the lower part of the movable support, the object lens is disposed on the pipe diameter unit and is correspondingly disposed below the illuminating elements, the photosensitive element is disposed in the pipe diameter unit and configured to collect a light source signal on the object lens, the A/D converting unit is connected to the photosensitive element, the control module is connected to the A/D converting unit;

the control platform is connected to the dark field microscope for on-line observation of cell culture and the cell incubator shaker respectively;

the control module is connected to the control platform; and the power source provides electricity for the system.

2. The full-automatic cell culture system according to claim 1, characterized in that the illuminating elements comprise a round lamp holder, and a plurality of illuminating lamps disposed on the lamp holder and arranged as a plurality of concentric circles, and centers of circles of the concentric circles have the same position as the center of circle of the lamp holder.

3. The full-automatic cell culture system according to claim 2, characterized in that a distance from the lamp holder to the object lens is 10-30 cm.

4. The full-automatic cell culture system according to claim 3, characterized in that light sources of the illuminating lamps and the object lens form a dark field, which meets the illumination needs of the dark field.

5. The full-automatic cell culture system according to claim 2, characterized in that the illuminating lamps are LED lamps.

6. The full-automatic cell culture system according to claim 1, characterized in that the support base comprises a step-motor, a slide mechanism and a base, the slide mechanism comprises a slide block and a slide rail, the control module is connected to and controls the step-motor, the step-motor is connected to the slide block, the slide block is slidably connected to the base by the slide rail and can move horizontally, the movable support is disposed on the slide block.

7. The full-automatic cell culture system according to claim 1, characterized in that the arc-shaped bottom plate is provided with one or a plurality of accessory fixing hole positions, and spaces for mounting or inserting external accessories are provided below the accessory fixing hole positions.

8. The full-automatic cell culture system according to claim 1, characterized in that the arc-shaped bottom plate is provided with a heating plate.

9. The full-automatic cell culture system according to claim 1, characterized in that the edge of the arc-shaped bottom plate is provided with baffles.

10. The full-automatic cell culture system according to claim 1, characterized in that the cell culture bag fixing parts are disposed on two sides of the arc-shaped bottom plate and comprise a platform extending from two sides of the arc-shaped bottom plate in horizontal direction, and the platform is provided with fixing rod clamps and/or fixing rod inserting mechanisms.

11. The full-automatic cell culture system according to claim 1, characterized in that the swing base is a flat plate and is provided with support arms on two ends, the culture bag support frame makes no contact with the swing base, and a clearance is provided therebetween for mounting or inserting the external accessory.

12. The full-automatic cell culture system according to claim 1, characterized in that the swing components comprise hinging seats and at least one vertical reciprocating movement mechanism, the hinging seats are disposed on the substrate, the swing base is hinged to the hinging seats, and the vertical reciprocating movement mechanism is connected to or abutted against the swing base.

13. The full-automatic cell culture system according to claim 1, characterized in that the cell culture bag comprises fixing parts on both sides of the bag body, the top surface of the closed bag body is provided with an external liquid adding port, an external liquid injecting port, a gas inlet and a gas outlet, the bottom surface of the closed bag body is provided with a liquid recycling port and at least one sensor connector, and each of the external liquid adding port, the external liquid injecting port, the gas inlet, the gas outlet, and the liquid recycling port is provided with an aseptic quick connector.

14. The full-automatic cell culture system according to claim 13, characterized in that the closed bag body is a three-dimensional bag cavity defined by an upper bag piece, a lower bag piece, a left side bag piece and a right side bag piece, the lower bottom sides of the left side bag piece and the right side bag piece are arc-shaped, the left side bag piece and the right side bag piece are oval, and the upper bag piece and the lower bag piece are rectangular.

15. The full-automatic cell culture system according to claim 13, characterized in that an innermost layer of the closed bag body is a polyethylene layer.

16. The full-automatic cell culture system according to claim 13, characterized in that materials of the closed bag body have a five-layer composite structure which comprises the polyethylene layer, an adhesive layer, an ethylene vinyl alcohol layer, another adhesive layer and another polyethylene layer from inside to outside in sequence.

17. The full-automatic cell culture system according to claim 13, characterized in that a number of sensor connectors is one or more.

18. The full-automatic cell culture system according to claim 17, characterized in that the sensor connectors are non-contact sensor connectors or contact sensor connectors.

19. The full-automatic cell culture system according to claim 18, characterized in that the non-contact sensor connector comprises a basal disc and a cavity containing sensor probe, the basal disc is provided with a transparent partition, the cavity containing sensor probe is connected to the basal disc, the basal disc and the cavity containing sensor probe are located on one side of the transparent partition, and the other side of the transparent partition is provided with a converting film.

20. The full-automatic cell culture system according to claim 19, characterized in that the converting film is a pH-induced color change film or dissolved oxygen-induced color change film.

21. The full-automatic cell culture system according to claim 1, characterized in that the control platform is provided with integrated circuit boards, and the integrated circuit boards are at least connected to the dark field microscope and the cell incubator shaker respectively, and the integrated circuit boards are connected to the control module.

22. The full-automatic cell culture system according to claim 21, characterized in that the control platform is further provided with one or more of the following:
    1) a flow control element of a cell culture fluid pipeline configured to provide cell culture fluid for the cell culture bag;
    2) a gas mixing unit providing gases for the cell culture bag, wherein a flow control element is provided in the gas mixing unit;
    3) an automatic heating unit for preheating the cell culture fluid;
    4) a pH detector and a dissolved oxygen detector; and
    5) a display screen.

23. The full-automatic cell culture system according to claim 22, characterized in that the integrated circuit boards of the control platform also meet one or more of the following requirements:
    1) the integrated circuit boards are connected to the shake device of the cell incubator shaker, to control a swing frequency and amplitude of the shaker;
    2) the integrated circuit boards are connected to a temperature control element on the cell incubator shaker, to control the temperature control element to heat the cell culture bag according to a set temperature;
    3) the integrated circuit boards are connected to the flow control element of the cell culture fluid pipeline, to control the liquid flow of the cell culture fluid pipeline;
    4) the integrated circuit boards are connected to the flow control element of the gas mixing unit, to control the gas flow of a gas pipeline;
    5) the integrated circuit boards are connected to the automatic heating unit, so as to control the automatic heating unit to preheat the cell culture fluid according to a preset temperature;
    6) the integrated circuit boards are connected to the pH detector, to control the pH detector to be ON or OFF;
    7) the integrated circuit boards are connected to the dissolved oxygen detector, to control the dissolved oxygen detector to be ON or OFF; and
    8) the integrated circuit boards are connected to the display screen.

24. The full-automatic cell culture system according to claim 21, characterized in that the control platform also comprises a control cabinet, and an automatic heating unit, a preheating bag and peristaltic pumps which are disposed on the control cabinet; the automatic heating unit comprises a preheating plate, the preheating bag is disposed on the preheating plate, the peristaltic pumps comprise a first peristaltic pump and a second peristaltic pump, an inlet of the preheating bag is communicated with external cell culture fluid by a first pipeline, an outlet of the preheating bag is communicated with the cell culture bag by a second pipeline, the first peristaltic pump is connected to the first pipeline, the second peristaltic pump is connected to the second pipeline, and the automatic heating unit, the first peristaltic pump and the second peristaltic pump are connected to the control module.

25. The full-automatic cell culture system according to claim 24, characterized in that a gas mixing unit is further disposed in the control cabinet, a gas outlet of the gas mixing unit is communicated with the cell culture bag by a third pipeline, a gas inlet of the gas mixing unit is connected to an external gas source, and the gas mixing unit is connected to the control module.

26. The full-automatic cell culture system according to claim 24, characterized in that the control cabinet is further provided with a pH value detection connector and a dissolved oxygen detection connector, and the pH value detection connector and the dissolved oxygen detection connector are connected to the control module and the cell culture bag.

27. The full-automatic cell culture system according to claim 1, characterized in that the control module comprises:
   a movable support control unit, configured to control the movement of the movable support;
   an illuminating element control unit, configured to control the illuminating element to be ON or OFF;
   a checking unit, configured to check content observed by the object lens under a current state, and parameters of a cell growth environment under the current state;
   a memory unit, configured to store the observed content which needs to be stored and record the parameters of the cell growth environment;
   a gas control unit, configured to control gas delivery in the cell culture bag; and
   a cell culture fluid control unit, configured to control the temperature and supply of cell culture fluid.

28. The full-automatic cell culture system according to claim 27, characterized in that the control module further comprises one or more of the following:
   a cell incubator shaker control unit, configured to set a frequency and a swing amplitude of the cell incubator shaker and a heating temperature for the cell culture fluid; and
   a control platform display unit, connected to a display screen of the control platform to set displayed content.

* * * * *